(12) United States Patent
Anazawa et al.

(10) Patent No.: US 7,223,326 B2
(45) Date of Patent: May 29, 2007

(54) CAPILLARY ELECTROPHORESIS SYSTEM

(75) Inventors: Takashi Anazawa, Kodaira (JP);
Takashi Irie, Musashimurayama (JP);
Masao Kamahori, Kokubunji (JP)

(73) Assignee: Hitachi, Ltd., Tokyo (JP)

( * ) Notice: Subject to any disclaimer, the term of this patent is extended or adjusted under 35 U.S.C. 154(b) by 862 days.

(21) Appl. No.: 10/609,554

(22) Filed: Jul. 1, 2003

(65) Prior Publication Data
US 2004/0003997 A1 Jan. 8, 2004

Related U.S. Application Data

(63) Continuation of application No. 09/696,262, filed on Oct. 26, 2000, now Pat. No. 6,635,164.

(30) Foreign Application Priority Data

Oct. 29, 1999 (JP) ................................. 11-307989

(51) Int. Cl.
*G01N 27/453* (2006.01)
(52) U.S. Cl. ........................ 204/601; 204/603; 204/605
(58) Field of Classification Search ........ 204/451–455, 204/601–605
See application file for complete search history.

(56) References Cited

U.S. PATENT DOCUMENTS

| 5,790,727 A | 8/1998 | Dhadwal et al. |
|---|---|---|
| 5,833,827 A | 11/1998 | Anazawa et al. |
| 5,856,100 A | 1/1999 | Hayashizaki |
| 5,883,827 A | 3/1999 | Morgan |
| 5,916,428 A | 6/1999 | Kane et al. |
| 6,048,444 A | 4/2000 | Takahashi et al. |
| 6,103,083 A * | 8/2000 | Merenkova et al. ........ 204/603 |
| 6,120,667 A | 9/2000 | Hayashizaki et al. |
| 6,132,582 A | 10/2000 | King et al. |

(Continued)

FOREIGN PATENT DOCUMENTS

JP 09-325130 6/1996

(Continued)

OTHER PUBLICATIONS

JPO computer translation of JP 2000-227413 A.*

(Continued)

*Primary Examiner*—Alex Noguerola
(74) *Attorney, Agent, or Firm*—Reed Smith LLP; Stanley P. Fisher, Esq.; Juan Carlos A. Marquez, Esq.

(57) ABSTRACT

A capillary electrophoresis system includes a plurality of capillaries arranged in parallel on a vertical plane at an identical distance from each other, each of which has a sample injection end immersed in a cathode buffer 23 and pointed downward vertically to facilitate connection between the cathode buffer 23 and a sample solution. The sample elution end is connected via a pump block 11 and a connection tube 3 to an anode buffer 24. The height is made identical between the liquid levels for buffers 23 and 24 to prevent movement of the separation medium in the capillaries. The sample introduced from the sample injection end 20 moves upward vertically via electrophoresis to the sample elution end in the capillary and is passed through and detected at the fluorescence detection position 19. The effective separation length is thus decreased to 10 cm or less to attain high throughput.

18 Claims, 16 Drawing Sheets

FOREIGN PATENT DOCUMENTS

| | | | |
|---|---|---|---|
| JP | 11-230936 | | 2/1998 |
| JP | 11-230940 | | 2/1998 |
| JP | 2000-227413 A | * | 8/2000 |
| WO | WO 95/21378 | | 2/1995 |

OTHER PUBLICATIONS

Howard Drossman, John A. Luckey, Anthony J. Kostichka, Jonathjan D'Cunha and Lloyd M. Smith, "High-Speed Separations of DNA Sequencing Reactions by Capillary Electrophoresis", Anal. Chem. 1990, vol. 62, pp. 900-903.

Mary Margaret Murphy, John J. O'Dea, Dieter Arn and Janet G. Osteryoung, "Theory for Cyclic Staircase Voltammetry for First-Order Coupled Reactions", Anal. Chem. 1990, vol. 62, pp. 903-909.

Dr. David N. Heiger, "High Performance Capillary Electrophoresis—An Introduction", 3rd Edition, pp. 78-84, 1997.

* cited by examiner

US 7,223,326 B2

CAPILLARY ELECTROPHORESIS SYSTEM

This application is a continuation application of U.S. application Ser. No. 09/696,262 filed on Oct. 26, 2000, now U.S. Pat. No. 6,635,164 B1.

BACKGROUND OF THE INVENTION

1. Field of the Invention

The present invention pertains to the field of analysis and separation of DNA, RNA and proteins. In particular, the present invention refers to an apparatus that allows for the separation and analysis of DNA, RNA and proteins.

2. Description of the Related Art

This invention concerns an apparatus for separating and analyzing DNA, RNA and proteins. Particularly, it relates to a capillary electrophoresis system effective to sequencing of DNA and RNA or, measurement of polymorphism, based on the versatility of individuals.

Analyzing technology for DNA and RNA has become important more and more in medical and biological fields concerning DNA analysis and DNA diagnosis. DNA analyzers at high speed and high throughput have been developed in relation with genome projects.

Capillary electrophoresis is a method of high speed and high resolution since higher electric fields can be applied due to high electric resistance and high efficiency of heat dissipation compared with slab gel electrophoresis. (Anal. Chem. 62, 900 (1999) (Prior art 1)).

As shown in FIG. 16, an electrophoresis system using a single capillary is known (Prior art 2: WO95/21378). The prior art 2 includes the following descriptions regarding FIG. 1. Nucleic acid fragments are electrophoretically separated in a capillary 134 filled with a flowing polymer solution as an electrophoretic separation medium. The temperature of the capillary during electrophoresis is an important parameter that gives an effect on both the extent of denaturation of samples and the separation speed of fragments. An elevated temperature can be used for lowering the viscosity of the separation medium during introduction of the separation medium into the capillary, to shorten the time of filling. A temperature control unit 130 is used for keeping the capillary 134 filled with the electrophoretic separation medium to a predetermined temperature. Since the resolution and the electrophoresis time are determined partially based on the length of the capillary, the temperature control unit contains a portion of the capillary for the length from 30 to 35 cm. The temperature of the capillary is controlled by using an insulated pressure plate and bringing the capillary in contact with a thermally controlled surface.

A sample is introduced into the capillary 134 filled with the separation medium. A sample injection end 142 of the capillary 134 and a cathode 150 are immersed in a sample 158 contained in a sample container 126 disposed to an auto-sampler 166, a sample elution end 138 of the capillary 134 and an anode 146 are immersed in an electrophoretic buffer 154 contained in an electrode vessel 118 and the sample is introduced into the capillary by application of electric field. An injection voltage is applied to the capillary by a power supply unit 122 connected to the anode 146 and the cathode 150. The injection voltage and injection time are controlled by a computer 174. After the injection of the sample into the capillary, electrophoretic separation is conducted.

The auto-sampler 176 changes the position for the sample injection end 142 of the capillary 134 and the cathode 150 from the container 126 containing the sample 158 to a container 170 containing an electrophoretic buffer 182. A voltage is applied to the capillary 124 by the power supply unit 122 connected to the anode 146 and the cathode 150, and sample ingredients pass the capillary by electrophoresis depending on the size thereof.

In order to avoid abnormality in fragment phoresis by siphoning of the electrophoresis medium, it is important to keep the liquid levels of the buffer identical between the container 170 and the container 118 during electrophoretic separation.

The fragment is detected after the separation by a detection unit 162. The detector used herein can include (1) a unit for spectrally separating an emission light (such as a grating or a prism), (2) an array of a plurality of detection elements sensitive to irradiation of light (e.g., diode array, CCD, photomultiplier), (3) an excited light source (e.g., incandescent lamp, arc lamp, laser, laser diode) and (4) a spectral array fluorescence detector using an optical system enabling directionation and conditioning for both of excited light and emitted light.

Before electrophoretic separation of the next sample, the electrophoresis medium in the capillary is replaced with a new one. There are described two methods of replacing the inside of the capillary with the new electrophoresis medium. In one method, the electrophoresis medium is replaced by the following procedures. A positive pressure from a pump 104 is applied to a container 108 containing a new electrophoresis medium and the medium is pumped out from the vessel 108 to a tee 111. Since a valve 112 is closed at this instance, the new electrophoresis medium flows mainly to a sample injection end 142. After the capillary is filled with the new electrophoresis medium between the sample injection end 142 and the tee 111, the valve 112 is opened and a new electrophoresis medium flows from the container 108 to a container 118 for containing a buffer. As a result, the capillary is completely filled with the electrophoresis medium between the sample injection end 142 and the sampling elution end 138. Since the length of the capillary between the sample elution end 138 and the tee 111 is shorter than the length of the capillary between the sample injection end 142 and the tee 111, when the valve 112 is opened to apply a pressure to the container 108, the new electrophoresis medium flows mainly to the sample elution end 138. After the capillary is filled with the new electrophoresis medium between the sample injection end 142 and the sample elution end 138, the valve 112 is opened so as to connect the sample injection end 142 and the sample elution end 138 to form a current path between electrodes 146 and 150. The foregoing provides an are explanation for FIG. 1 of the prior art 2.

An electrophoresis system for DNA using a single capillary is supplied as a commercial product from Perkin Elmer Co. (name of product: ABI Prism 310). A high throughput system capable of analyzing a plurality of samples simultaneously, by arranging 96 capillaries into an array is supported as a commercial product from Perkin Elmer Co. (name of product: ABI Prism 3700).

In genome analysis, DNA fragments formed by finely fragmenting large size DNA, at random are read and an original DNA is read by joining the result of reading. As the DNA read length capable of being read by electrophoresis at one time is increased, the efficiency and the speed of the entire analysis also increase.

Accordingly, in the capillary electrophoresis system, a capillary of increased effective length is used so that long DNA can be read. For example, in ABI Prism 310 or ABI Prim 3700, 600 base lengths can be read in about two hours, by electrophoresis under standard conditions (200 V/cm, 50(C), by setting the effective separation length to 50 cm and using a polymer solution POP 6 supplied from Perkin Elmer Co.

As the speed, the throughput and the read length have been increased for the capillary electrophoresis systems, it is expected that the entire base sequencing of the human genome will be completed substantially in 2001. After the base sequences for the entire genome are found, the necessity for reading long DNA will be reduced. It will only be necessary to read specific regions on the genome.

For example, it has now been advanced in a large scale national project to investigate single nucleotide polymorphisms present on the genome, on every group of persons and examine the relationship thereof with diseases or reactivity to chemicals. In the featured medical treatment and new industries, it will be important to relate not only the single nucleotide polymorphism but also specific sequences with diseases or various phenotypes. It is also possible to examine the expressions in each of the organs and each of the states of individual persons, not just with the genome, based on cDNA sequencing. Since a number of samples such as various persons, various diseases and various organs have to be analyzed, it is necessary to outstandingly improve the analysis throughput of the system. In such DNA analyses, reading long base lengths is not necessary, but relatively short base lengths have to be read at high speed, with higher throughput.

However, the constitution of the system for analyzing a great amount of relatively short DNA is not considered in commercial products and an effective separation length as long as 50 cm has been used. When electrophoresis is conducted under standard conditions (200 V/cm, 50° C.), using POP 6 as the polymer solution, a plurality of samples can be electrophoresed serially at 65 min cycles to read 200 bases for each sample, which includes periods of 15 min for filling the polymer solution and pre-electrophoresis. When 96 capillaries are used (in ABI Prism 3700), the upper limit for the analysis is 2127 samples in 24 hours.

This invention intends to provide a high performance capillary electrophoresis system capable of conducting capillary electrophoresis, with short effective separation lengths stably capable of electrophoresis at high throughputs and ultrahigh speeds, and applicable to the separation and analysis of nucleic acids and proteins or the sequencing of nucleic acids, and further to measurements for polymorphism analysis, based on the versatility of base sequences of individuals.

BRIEF SUMMARY OF THE INVENTION

The present invention is a capillary electrophoresis system that consists of a capillary for separating fluorescently labeled samples by electrophoresis by applying a voltage across both ends of said capillary, an irradiation unit for irradiating a laser beam to the capillary and a detection unit for detecting fluorescence emitted from a plurality of electrophoretically separated samples. A relationship is maintained between the geometrical characteristics of the capillary: T the height of a highest position of the capillary in a vertical direction, measured from a reference horizontal plane, E1 the height of the sample injection end in vertical direction from the reference horizontal plane, and L1 the capillary length between the sample injection end and the fluorescence detection position at which the laser beam is irradiated. The relationship is T–E1>L1. The sample injection end points substantially vertically downward.

The capillary electrophoresis system further comprises a temperature controller that sets at least a part of the capillary at a selected temperature during electrophoresis. A line connecting the sample injection end and the fluorescence detection position is substantially parallel with a vertical line. Also, a line connecting the sample injection end and the sample elution end of the capillary is substantially parallel with a vertical line.

The capillary electrophoresis system further comprises an electrolyte vessel with a gas permeation membrane, and a tube connected to the gas permeation membrane. A plurality of gases are sucked from an electrolyte set that is part of the electrolyte vessel through the gas permeation membrane. The electrolyte vessel is on one side of the sample elution end and is sealed. A pressure equal or higher that the atmospheric pressure is applied to the electrolyte vessel on the sample injection end. The capillaries used are provided. The sample injection end, the plurality of fluorescence detection positions and the sample elution end are arranged substantially at an identical distances from each other, on an identical plane.

Further, in a different embodiment of the invention, a capillary electrophoresis system comprises a capillary containing a solution of an electrophoretic separation medium for separating fluorescent-labeled samples using electrophoresis created by applying a voltage across both ends of said capillary and an irradiation unit for irradiating a laser beam on to the capillary. The capilarity has a fluorescence detection position at which a laser beam is irradiated. The movements of a plurality of samples placed at the fluorescence detection position are directed vertically upward, while the laser beam is irradiated.

The capillary electrophoresis system further comprises a temperature controller that sets at least a part of the capillary at a selected temperature during electrophoresis. A a line connecting a sample injection end and a fluorescence detection position is substantially parallel with a vertical line. Also, a line connecting a sample injection end and a sample elution end of the capillary is substantially parallel with a vertical line.

The capillary electrophoresis system further comprises an electrolyte vessel with a gas permeation membrane and a tube connected to the gas permeation membrane. The gases are sucked from an electrolyte set into the electrolyte vessel through the gas permeation membrane. The electrolyte vessel is on one side of the sample elution end and is sealed. A pressure equal or higher that atmospheric pressure is applied to the electrolyte vessel onto the sample injection end. The capillaries are provided. The sample injection end, said fluorescence detection positions and said sample elution end are arranged substantially at identical distances on one identical plane.

Yet, a further embodiment of the present invention is a capillary electrophoresis system comprising a capillary for separating a plurality of fluorescently-labeled samples by electrophoresis by applying a voltage across both ends of the capillary, means for introducing an electrophoretic separation medium into the capillary and for removing the electrophoretic separation medium from the capillary, an irradiation unit for irradiating a laser beam to the capillary and a detection unit for detecting fluorescence emitted from a plurality of samples that are electrophoretically separated.

A relationship is maintained between the geometrical characteristics of the capillary: T the height of a highest position of the capillary in a vertical direction, measured from a reference horizontal plane, E1 the height of the sample injection end in vertical direction from the reference horizontal plane, and L1 the capillary length between the sample injection end and the fluorescence detection position at which the laser beam is irradiated. The relationship is T−E1>L1. The sample injection end points substantially vertically downward.

Another embodiment of the present invention is a capillary electrophoresis system comprising a capillary for containing a solution of an electrophoretic separation medium for separating fluorescently-labeled samples by electrophoresis by applying a voltage across both ends of the capillary, means for introducing the solution into the capillary and removing the solution from the capillary, an irradiation unit for irradiating a laser beam onto the capillary, a detection unit for detecting fluorescence emitted from a plurality of samples that are electrophoretically separated. The capillary has a fluorescence detection position where the laser beam is irradiated. The movements of the samples at the fluorescence detection position are substantially vertically upward.

Further features and advantages of the invention, as well as the structure and operation of various embodiments of the invention, are described in detail below, with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS

Other objects and advantages of the invention will become apparent during the following discussion of the accompanying drawings, wherein.

DETAILED DESCRIPTION OF THE INVENTION

Figure 1:
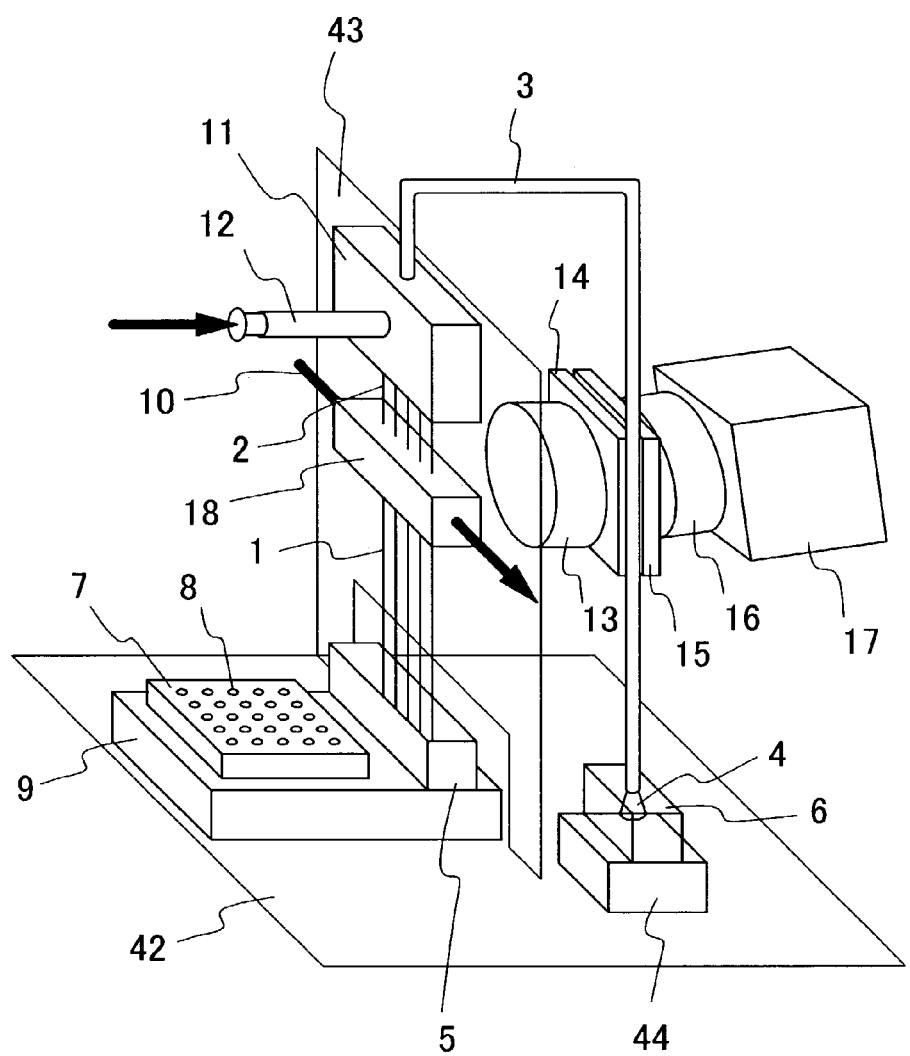
FIG. 1 is a perspective view illustrating an example of an entire constitution for a first device of Example 1 according to this invention.

Definitions for the terms and symbols to be used in the following explanations are shown below.

"sample injection end 20" means one end of a capillary to which a sample is introduced.

"sample elution end 21" means the other end of the capillary from which the sample is eluted.

"fluorescence detection position 19" means a position of the capillary where a laser beam 10 is irradiated and fluorescence is detected.

"separation part 1" means a portion of the capillary in a section between the sample injection end 20 and the fluorescence detection position 19.

"sample elution part 2" means a portion of the capillary in a section between the fluorescence detection position 19 and the sample elution end 21.

"Effective separation length L1" means the length of the capillary in the separation part 1. "Sample elution length L2" means the length of the capillary in the sample elution part 2.

"Entire capillary length" is (L1+L2). "Reference horizontal plane W" means horizontal reference plane.

"E1" shows a height from the reference horizontal plane W to the sample injection end 20.

"E2" shows a height from the reference horizontal plane W to the sample elution end 21.

"D" shows a height for the fluorescence detection position 19 from the reference horizontal plane W.

"T" shows the maximum height of the capillary from the reference horizon plane W.

"B1" shows a height from the reference horizontal plane W to the liquid level of the cathode buffer 23.

"B2" shows a height from the reference horizontal plane W to the liquid level of the anode buffer 24.

"S" shows a height for the position of the pressure-resistant valve 4 from the reference horizontal plane which is used for sealing the pump block 11 or the connection tube 3.

This invention provides an electrophoresis system using identical components and a polymer solution with those of the capillary electrophoresis system of the prior art 2 and arranging capillaries of short effective lengths into an array. The present inventor has made various studies on the constitution for realizing high speed electrophoretic analysis by using the capillaries of short effective lengths and, as a result, has found the following constitution.

A plurality of capillaries filled with a polymer solution are arranged with sample injection ends being pointed downward vertically, sample elution ends being pointed upward vertically, and the axis for each of the capillaries being in parallel with a vertical line. The sample injection ends are pointed downward vertically because of the same reason as that for the prior art, namely, so that the sample injection ends can be immersed in the cathode buffer and the sample solution by the operation of the auto-sampler.

Fluorescence detection positions are disposed between the sample injection ends and the sample elution ends. That is, in a state where the samples introduced from the sample injection ends are moved vertically upward by electrophoresis in the capillaries, a laser beam is irradiated to each of the capillaries to conduct fluorescence detection simultaneously. With such an arrangement, the effective separation length of the capillary can be shortened to 10 cm or less.

The sample elution end of each of the capillaries is connected to a polymer solution containing container filled with a polymer solution. A pump capable of applying pressure to the polymer solution in the inside is connected with the polymer solution containing container. Further, the polymer solution containing container is connected with one end of a connection tube filled with the polymer solution and a pressure resistant valve is disposed to the other end of the connection tube. The inner diameter of the connection tube is made larger than the inner diameter of the capillary.

The sample injection end of each of the capillaries is immersed in a cathode buffer and the end of the connection tube attached with a pressure resistant valve is immersed in an anode buffer. When the pressure resistant valve is opened, the cathode buffer, the polymer solution in each capillary, the polymer solution in the polymer solution containing container, the polymer solution in the connection tube and the anode buffer are electrically connected and a flow channel is formed. During electrophoresis, flow of the polymer solution in each of the capillaries can be prevented by making the height of the liquid levels identical between both of the buffers.

Procedures for electrophoresis are identical with those in the prior art 2. The pressure resistant valve is kept open, the auto-sampler holding a cathode buffer vessel and a micro tighter plate having a plurality of sample solution vessels is operated and the sample injection ends of the respective capillaries are immersed in different sample solutions respectively. Each of the samples is electrophoretically injected into each of the capillaries by applying a constant voltage between each of the sample solutions and the anode buffer for a certain period of time. After the injection of the sample, the auto-sampler is operated to immerse each of the sample injection ends into the cathode buffer. A constant voltage is applied between the cathode buffer and the anode buffer to start electrophoresis.

A laser beam is irradiated on the fluorescence detection position for each of the capillaries, emitted fluorescence from the samples passing there are detected respectively and analyzed by a computer. After the completion of the electrophoresis, the polymer solutions in each of the capillaries is replaced for conducting electrophoresis for the next group of samples.

The pressure resistant valve is closed and the pump is operated to apply a pressure to the polymer solution in the polymer solution containing container. Thus, the polymer solution is filled from the elution ends and discharged from the injection ends, so that the polymer solution in the inside can be replaced. After filling the polymer solution, the pressure resistant value is opened, and sample injection and electrophoresis for next group of samples are conducted.

A typical constitution of this invention is to be explained below briefly with reference to FIG. 2. A plurality of capillaries are arranged each at an equal distance in parallel with the vertical line on a plane, with a sample injection end 20 to be immersed in a cathode buffer 23 being pointed downward vertically to facilitate connection between the cathode buffer 23 and a sample solution. A sample elution end 21 is connected by way of a pump block 11 and a connection tube 3 with an anode buffer 24. The liquid levels of both of the buffers 23 and 24 is made equal to prevent the separation medium in the capillary from movement. The sample introduced from the sample injection end 20 is moved upward vertically to the sample elution end 21 in the capillary, and passed through a fluorescence detection position 19 where fluorescence from the sample is detected. A high throughput capillary electrophoresis system with an effective separation length of 10 cm or less can be obtained.

In DNA analysis for analyzing a great amount of relatively short DNA, sequencing is conducted by amplifying only the aimed region on the genome. If a region to be analyzed can be restricted, the base length to be sequenced can be shorter by so much. In a case of analysis for single nucleotide polymorphism which has been found to be present on a specified position, sequencing for 10 base lengths may sometimes be sufficient. In most of application uses, sequencing 100 base lengths may be sufficient.

For example, when electrophoresis is conducted under standard condition (200 V/cm, 50(C), setting the effective separation length of electrophoresis to 10 cm and using POP 6 as the polymer solution, 200 base lengths can be read in about 10 min. Even when five minutes are required for filling of polymer and pre-electrophoresis, a plurality of samples can be electrophoresed serially in 15 minute cycles. When 96 capillaries are arranged in an array and electrophoresed in parallel, analysis is possible as much as for 384 samples in one hour and 9216 samples in 24 hours, which is much more higher than the throughput of the DNA analysis by the prior art.

EXAMPLE 1

FIG. 1 is a perspective view illustrating an example of an entire constitution for a first device of Example 1 according to this invention.

Example 1 shows a system using a polymer solution as a separation medium and capable of simultaneous electrophoresis by arranging a plurality of capillaries of short effective lengths into an array. FIG. 2 is a front elevation view illustrating an example of an entire constitution for the first device of Example 1 according to this invention (as viewed from the left in FIG. 1), which is a view from the direction vertical to the plane on which each of the capillaries is arranged. FIG. 3 is a side elevation view illustrating an example of an entire constitution for the first device of Example 1 according to this invention (as viewed from the right in FIG. 2), which is a view from the side relative to the plane on which each of the capillaries is arranged. FIG. 4 is a cross sectional view at a fluorescence detection position for the first device of Example 1 according to the this invention.

As shown in FIG. 1, axes of respective capillaries are arranged in parallel with a vertical direction and each at an equal distance on one identical plane. Intermediate portions in the longitudinal direction of the capillaries are contained in a quartz cell 18, and a laser beam 10 is irradiated in parallel with a plane on which axes for the respective capillaries are arranged. Each of the capillaries is partitioned into a separation part 1 and a sample elution part 2 with the position for each of the capillaries at which the laser bean 11 is irradiated (fluorescence detection position 19) as a boundary.

The lower end of the separation part 1 (sample injection end 20) is immersed in a cathode buffer vessel 5 containing a cathode buffer 23. The upper end of the sample elution part 2 (sample elution end 21) is connected with a pump block 11 having an internal space in which the polymer solution 25 is filled, and a polymer solution as an electrophoretic separation medium is filled in each of the capillaries from the sample elution end 21. An anode buffer vessel 6 for containing an anode buffer 24 and the pump block 11 are connected by way of a connection tube 3 filled with a polymer solution 27. Further, a gas tight syringe 12 is connected to the pump block 11 and used for applying pressure to the polymer solution in the pump block 11. A pressure resistant valve 4 used upon filling the polymer solution to each of the capillaries is connected to the top end of the connection tube 3 on the anode buffer 24 side.

Fluorescence emitted from the sample electrophoretically moving at each of the capillary positions (fluorescence detection position) irradiated with the laser beam 10 is formed into a parallel luminous flux by a first camera lens 13, passed through a laser light rejection filter 14, put to wavelength dispersion through a grating 15, focused by a second camera lens 16 and then detected by a 2-dimensional CCD camera 17. Since the direction of the wavelength dispersion is perpendicular to the direction of a line along which the fluorescence detection positions are arranged, wavelength dispersed images of fluorescence from each of the capillaries do not interfere with each other and fluorescence emitted from the sample electrophoretically moving in each of the capillaries can be detected simultaneously. Fluorescence signals are transferred to a computer (not illustrated) and analyzed.

Different sample solutions are contained in respective sample solution vessels 8 of a micro titer plate 7 having sample solution vessels (wells) 8 arranged in a lattice at an equal distance. An auto-sampler 9 on which the cathode buffer vessel 5 and the micro titer plate 7 are disposed is secured to a horizontal holder plate 42. The quartz cell 18 and the pump block 11 are secured to a vertical holder plate 43 and the vertical holder plate 43 is secured in parallel with the vertical direction to the horizontal holder plate 42. The surface of the horizontal holder plate 42 defines a reference horizontal plane.

The capillary has a 360 µm outer diameter, 50 µm inner diameter and a 20 cm entire length, and is made of fused silica. Each of the sample injection ends 20 is pointed downward vertically and aligned substantially while each of the sample elution ends 21 is pointed upward vertically and aligned substantially and capillaries are arranged at an equal distance (distance: 9 mm).

In this invention, there is no restriction for the number and the arrangement space for the capillaries to be formed into an array, and it is practically convenient to match the distance for the arrangement of the sample injection ends of the capillaries with that of the wells (sample solution vessels 8) of the micro titer plate 7.

In the sample preparation, a plurality of samples are treated collectively by using a micro titer plate of 12×8=96 wells and a micro titer plate with 24×16=384 wells. Accordingly, it will be very much convenient when the samples can be injected directly from the micro titer plate to the capillaries. For this purpose, the arrangement space for the sample injection ends of the capillaries is made equal with the arrangement distance for the wells (sample solution vessels) in the micro titer plate.

In Example 1, the arrangement space for the sample injection ends of twelve capillaries is made identical with the arrangement distance 9 mm for the wells in a 96 well micro titer plate. In a case of using a 384 well micro titer plate, the arrangement distance for the sample injection ends is set to 4.5 mm. In each of the drawings shown below, only the five capillaries are shown for the sake of simplicity.

Different sample solutions are contained in the respective sample solution vessels (wells) 8 of 12×8=96 arranged in a lattice at 9 mm distance. The direction of arranging twelve sample solution vessels 8 is made in parallel with the direction of arranging the sample injection ends 20. In FIG. 1, the sample solution vessels 8 arranged in a lattice manner on the micro titer plate 7 are shown only for 5×5=25 for the sake of simplicity.

The auto-sampler 9 comprises a driving stage having 2-axis driving mechanism and can be moved in two directions that is, a horizontal direction and a vertical direction. The auto-sampler 9 is driven in two directions, each of the sample injection ends 20 is immersed in the sample solution in twelve sample solution vessels, the sample is injected into each capillary from the sample injection end 20 and then the sample injection end 20 can be immersed in the cathode buffer 23 of the cathode buffer vessel 5 by the operation of the auto-sampler 9. During the electrophoresis, the height of the driving stage of the auto-sampler 9 is controlled so that the liquid level of the cathode buffer 23 in the cathode buffer vessel 5 secured to the auto-sampler 9 is identical with the liquid level of the anode buffer 24 in the anode buffer vessel 6 is identical. The anode buffer vessel 6 is disposed on an anode buffer vessel base 44, and the anode buffer vessel 44 is secured to the horizontal holding plate 42.

Figure 2:
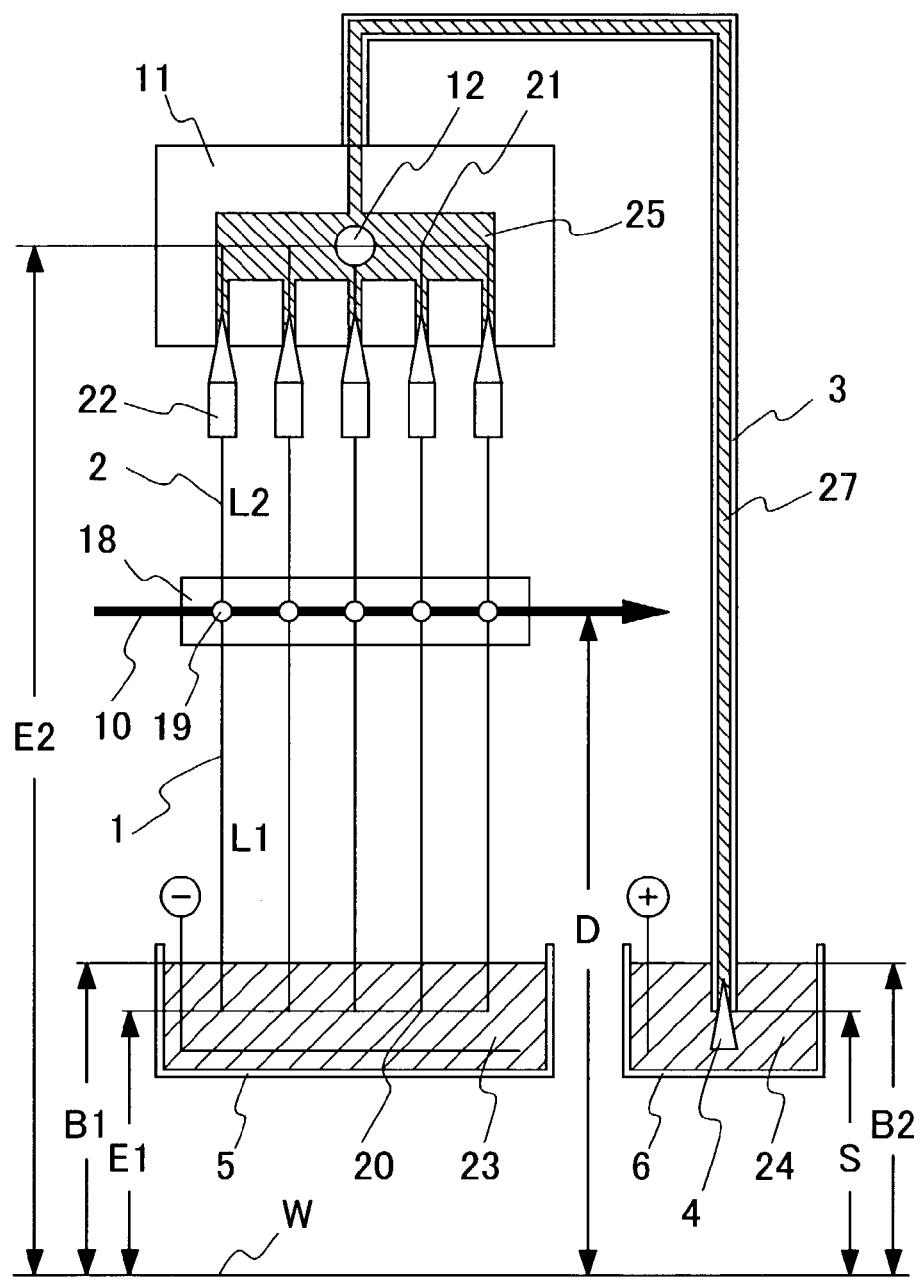
FIG. 2 is a front elevation view illustrating a first device of Example 1 according to this invention.
Figure 3:
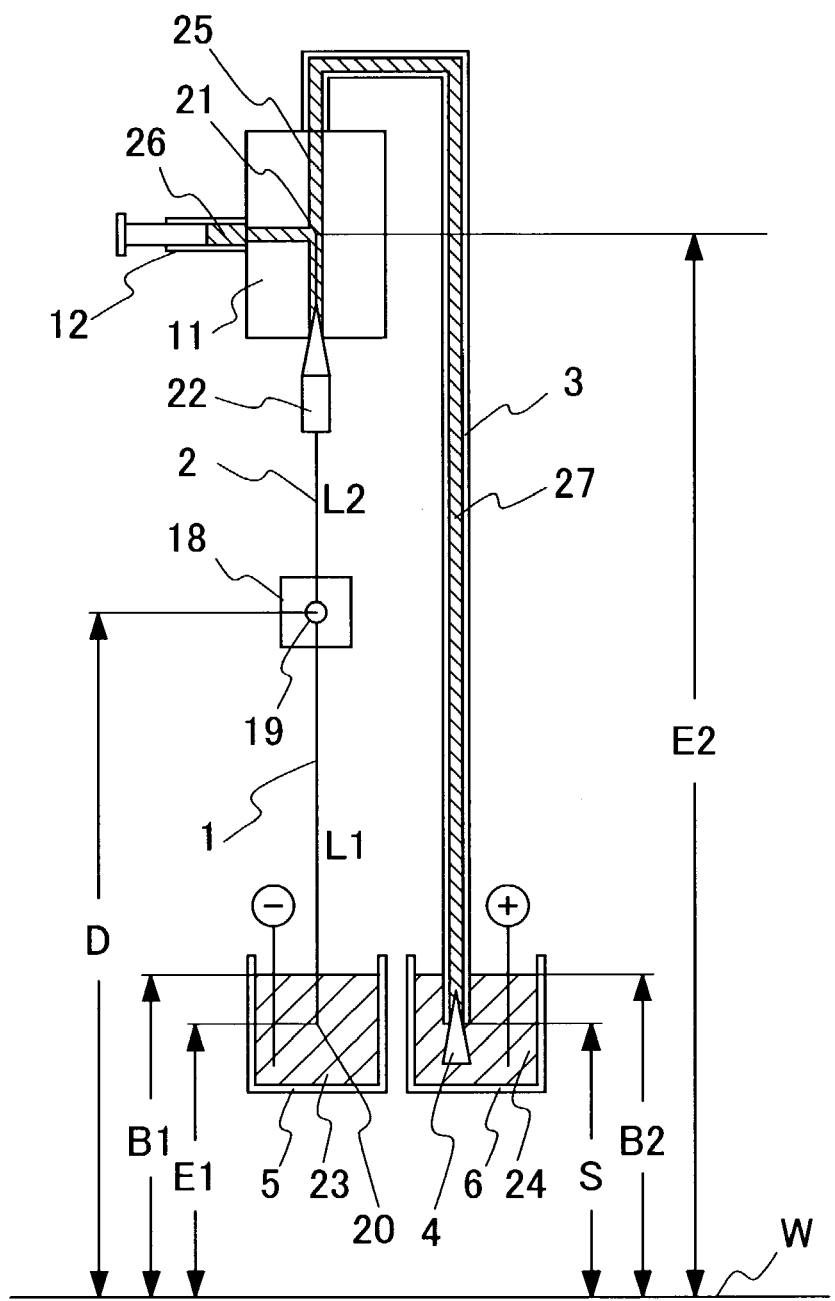
FIG. 3 is a side elevation view illustrating the first device of Example 1 according to this invention.
Figure 4:
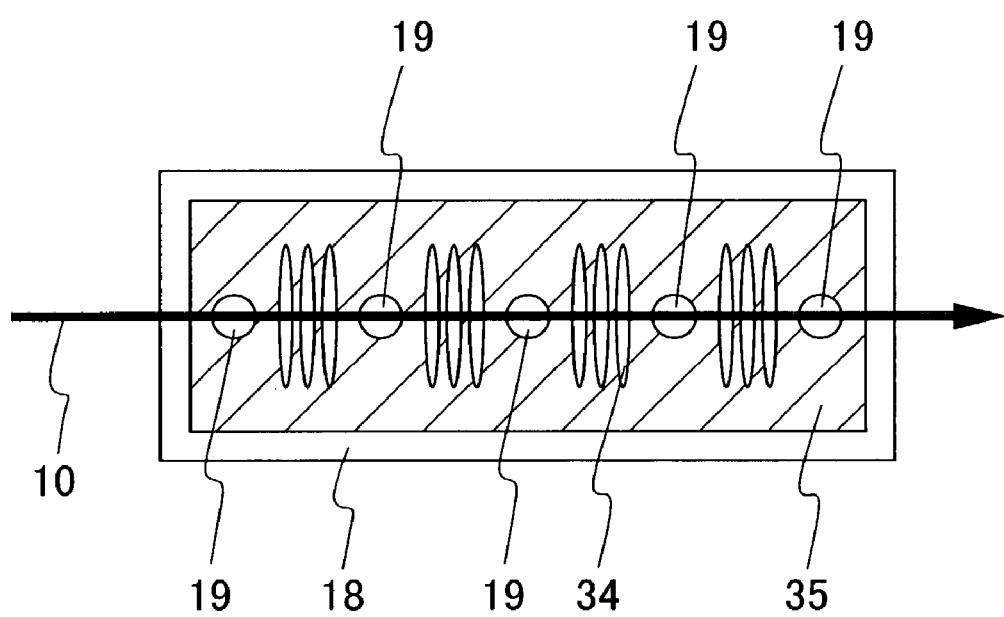
FIG. 4 is a cross sectional view at a fluorescence detection position of the first device of Example 1 according to the this invention.

As shown in FIG. 2 and FIG. 3, the sample injection ends 20 and the sample elution ends 21 are arranged, respectively, on two lines vertical to the axis of the capillary each at a 9 mm distance. A detection window is previously formed to each of the capillaries at a distance of 10 cm from the sample injection end 20 and at a distance of 10 cm from the sample elution end 21 to constitute a fluorescence detection position 19. The detection window is manufactured by removing a polyimide film covering the outer surface of the capillary by means of heating. The fluorescence detection positions 19 are arranged each at a 9 mm distance on one identical line which is vertical to the axis of each capillary. The sample injection ends 20, the fluorescence detection positions 19 and the sample elution ends 21 are respectively arranged substantially each at a equal distance (9 mm distance) on one identical plane. The effective separation length L1=10 cm and the sample elution length L2=10 cm.

FIG. 4 shows a cross sectional view including a laser beam 10 and vertical to the axis for each of the capillaries. The portions of the capillaries including the fluorescence detection positions 19 are contained in the quartz cell 18. The laser beam for exciting the fluorescence is condensed through a lens (not illustrated) to about 50 µm, and irradiated from the lateral side of the plane on which the capillaries are arranged along the line on which the fluorescence detection positions 19 are arranged.

A glycerol solution 35 is filled in the quartz cell 18, to suppress reflection of the laser beam 10 on the outer surface of the capillary at the fluorescence detection position 19. The refractive index of the glycerol solution 35 is substantially equal with the refractive index of the quartz. Since the laser beam permeating the capillary is converged by the concave lens action of the capillary it is re-condensed by using a condensing lens 34 (Electrophoresis 20, 539-546 (199)(prior art 3)).

Condensing lenses 34 are disposed each by three between each of the fluorescence detection positions 19 of the capillaries, such that the center axis for each of the condensing lenses 24 is aligned with the line along which the fluorescence detection positions 19 are arranged and with the irradiation axis of the laser beam. Since the condensing lenses 34 are immersed in the glycerol solution, the material for the condensing lens 34 used has a higher refractive index than that of quartz in order to provide a condensing action. With the constitutions described above, the laser can be irradiated to each of the fluorescence detection positions 19 with no decay for the intensity of the laser beam. The samples introduced from the sample injection ends 20 move upward vertically to the sample elution ends 21 by electrophoresis, undergo laser beam irradiation in the course of movement and emit fluorescence.

As shown in FIG. 2 and FIG. 3, the sample elution ends 21 are arranged in an internal space filled with the polymer solution of the pump block 11 made of acrylic resin. By pressure resistant connection of each of the capillaries, the connection tube 3 and the gas tight syringe 12 to the pump block 11, a constitution for introducing the polymer solution 25 into each of the capillaries is formed. The pump block 11 is formed with a first fine hole penetrating the internal space in the direction of connecting the sample elution end 21 and the sample injection ends 20 of each of the capillaries and a second fine hole for connecting the internal space with the gas tight syringe 12. The line connecting each of the sample elution ends 21 passes through the central axis of the second fine hole.

The pressure resistant connection means that when high pressure is applied to the polymer solution 25 in the pump block 11, the polymer solution 25 does not leak from each of the connected portions to the outside of the pump block 11. Polymer solutions 26, 27 are filled in the gas tight syringe 12 and in the connection tube 3 respectively. It is adapted such that air scarcely intrudes in the polymer solution 25 in the pump block 11, the polymer solution 27 in the connection tube 3 and the polymer solution 26 in the gas tight syringe 12.

As shown in FIG. 2 and FIG. 3, the sample elution ends 21 are connected by connectors 22 with the pump block 11 in a pressure resistant manner. The connector 22 is a male thread made of plastic material having a small hole at a center of such a size as just allowing a capillary to pass therethrough and pointed conically toward the top end. The pump block 11 has a tapered female threaded hole mating the connector 22. The top end of the female threaded hole is in communication with the internal space in the pump block 11 filled with the polymer solution 25.

After passing the capillary through the center hole of the connector 22, it is passed through the tapered female thread hole and then the male thread is clamped into the tapered female threaded hole. Then, the top end of the male thread is deformed by a collision of the top end of the male thread with the top end of the female threaded hole. As a result, a gap between the connector 22 and the capillary and a gap between the connector 22 and pump block 11 are sealed. Since the seal is secured by the threads, even when the inside of the pump block 11 is put to a high pressure state at several tens atm, the polymer solution 25 does not leak through the gaps.

The connection tube 3 is a pressure resistant tube which is made of a freely bendable material such as a polytetrafluoroethylene resin. The top end of the connection tube 3 opposite to the pump block 11 is extended downward and immersed in the anode solution 24 in the anode solution vessel 6. A pressure resistant valve 4 is connected to the top end of the connection tube 3. When the pressure resistant valve 4 is closed, the top end of the connection tube 3 is sealed. The sealed position is in the anode buffer. The anode buffer vessel 6 is placed on the anode buffer vessel stand 44 such that the liquid level of the anode buffer 23 is identical with the liquid level of the cathode buffer 24.

When the pressure resistant valve 4 is closed and the piston of the gas tight syringe 12 is driven by using an external motor (not illustrated) in the direction of an arrow shown in FIG. 1, pressure of the polymer solutions 25, 26, 27 is increased. As a result, the polymer solution 25 is filled in the capillary from the sample elution end 21 to the sample injection end 20.

For controlling the temperature of the capillary, air previously controlled to a predetermined temperature is blown from the direction vertical to the plane on which capillaries are arranged (from this side in FIG. 2) to each of the capillaries (device for blowing temperature controlled air is not illustrated in FIG. 1).

Actual procedures for electrophoresis are to be explained below. It is an aim of this experiment to statistically examine the correlationship between single nucleotide polymorphisms the presence of which at specified positions on the genome has been known and various kinds of diseases. For each of eight types of diseases, blood is collected from twelve patients, from which genomes are extracted. For each of the samples, only 200 base length in the region including and near the position for the single nucleotide polymorphism are amplified to conduct DNA sequencing reaction and possessed in 12×8 sample solution vessels 8 of the micro titer plate 7 having 12×8 sample solution vessels 8.

For the DNA sequence reaction, a Big Dye Terminator Cycle Sequencing FS Ready Reaction Kit sold from Perkin Elmer Co. is used. For the polymer solution and the buffer, POP 6, 310 Genetic Analyzer Buffer with EDTA sold from the company respectively are used.

The temperature of air blown to each of the capillaries is set to 50° C. to control the temperature for each of the capillaries to 50° C.

The pressure resistant valve 4 is closed, the piston of the gas tight syringe 12 is driven to apply a pressure at 25 atm to the polymer solution 25 in the pump block 11 to fill the polymer solution to each of the capillaries. After keeping the high pressure state for 5 min, driving for the piston is stopped and the pressure resistant valve 4 is returned to an open state to release the high pressure state. By the above step, in each of the capillaries, a polymer solution about twice as much as the inner volume of each of the capillaries is replaced.

Each of the sample injection ends 20 is immersed into the cathode buffer 23, and pre-electrophoresis is conducted by applying a high voltage at 4 kV across both ends of the capillaries, setting the cathode buffer 23 to a high negative voltage and grounding the anode buffer 23 to the earth. Since the inner cross sectional area of the connection tube 3 is large enough compared with the inner cross sectional area of the capillary, the voltage applied to both of the buffers is applied as it is to both ends of the capillaries. The entire length of the capillaries is 20 cm and the electric field intensity is 200 V/cm.

After the end of the pre-electrophoresis, the auto-sampler 9 is driven to immerse each of the sample injection ends 20 to the sample solution in twelve sample solution vessels 8 of the micro titer plate 7. The samples are injected while applying a high voltage at 0.8 kV for 30 sec across both ends of the capillaries while setting each of the sample solutions to a high negative voltage and grounding the anode buffer 24 to the earth. In this case, electric field intensity is 40 V/cm.

After the sample injection, the auto-sampler 9 is driven again to immerse the sample injection ends 20 into the cathode buffer 23 and initial electrophoresis is conducted by applying a high voltage at 0.5 kV across both end of the capillaries for 5 min while setting the cathode buffer 23 to a high negative voltage and grounding the anode buffer 24 to the earth. Then, the application voltage is elevated to 4 kV to start electrophoresis.

An Ar ion laser beam (oscillating at 488 nm and 515 nm with 20 mW power) is used as the laser beam 10 and the Ar ion laser beam is irradiated at the fluorescence detection position 19 for each of the capillaries. The 2-dimensional CCD camera 17 is controlled by the computer, and fluorescence emitted from the sample under electrophoretic movement in each of the capillaries is continuously detected at a sampling interval of 0.1 sec and recorded. After conducting electrophoresis continuously for 10 min, the fluorescence detection and the voltage application are stopped. The result of the electrophoresis is analyzed by the computer and displayed and recorded.

Successively, for analyzing the next twelve samples, the same procedures as described above of filling the polymer solution, pre-electrophoresis, sample injection, initial electrophoresis and electrophoresis are repeated. Since twelve samples can be electrophoresed in 20 min by one cycle, electrophoresis for 96 samples is completed in 160 min.

In Example 1, capillaries of specified size have been used but similar effects can also be obtained by using the capillaries of other sizes. Further, an example of using the capillaries by the number of 12 is shown but the same constitution as that in Example 1 is possible and a similar effect can be obtained by using one or more arbitrary number of capillaries.

Further, while POP 6 is used as the polymer solution for the separation medium, polymer solutions of other types may also be used. Electrophoretic separation can of course be conducted in the same constitution of the system as in Example 1 using a crosslinked gel for the separation medium. Electrophoresis may also be conducted by using a solution not containing the polymer in the capillary.

The constitution of the system in Example 1 has a feature in satisfying the following (condition 1 to condition 5) simultaneously.

(Condition 1): Electrophoresis is conducted after filling the polymer solution or an aqueous solution into the capillary.
(Condition 2): The height for the liquid level of the anode buffer in the anode buffer vessel is substantially identical with the height of the liquid level of the cathode buffer in the cathode buffer vessel.
(Condition 3): The sample injection end of the capillary is substantially pointed downward vertically.
(Condition 4): The sample injected from the sample injection end of the capillary moves upward vertically in the capillary at least in the initial stage by the electrophoresis.
(Condition 5): The sample undergoes laser irradiation during upward vertical movement in the capillary by which fluorescence is detected.

When W, E1, E2, D, T (T=E2 in the examples shown in FIG. 2 and FIG. 3), B1, B2 and S defined previously are used, (condition 2) is expressed as relation 1 and (condition 5) is expressed as relation 2.

$$B1=B2 \qquad \text{relation 1}$$

$$T-E1>L1 \qquad \text{relation 2}$$

The condition where the sample elution end is at a position higher than the fluorescence detection position is expressed by relation 3, the condition where the sample elution end is at the highest position is expressed by relation 4 and the condition where the position that the pressure resistant valve seals the connection tube is present in the anode buffer is expressed by relation 5.

$$E1 \square \dagger D \qquad \text{relation 3}$$

$$T=E2 \qquad \text{relation 4}$$

$$S \square \ldots B2 \qquad \text{relation 5}$$

The first device in Example 1 has a problem in that the light condensing efficiency and the spectral accuracy regarding the capillaries disposed on both ends in the array are lowered compared with the light condensing efficiency and the spectral accuracy regarding the capillaries disposed at a central portion in the array. Further, for collectively irradiating the laser beam, the quartz cell 18 shown in FIG. 4 is required, which somewhat complicates the system.

Figure 5:
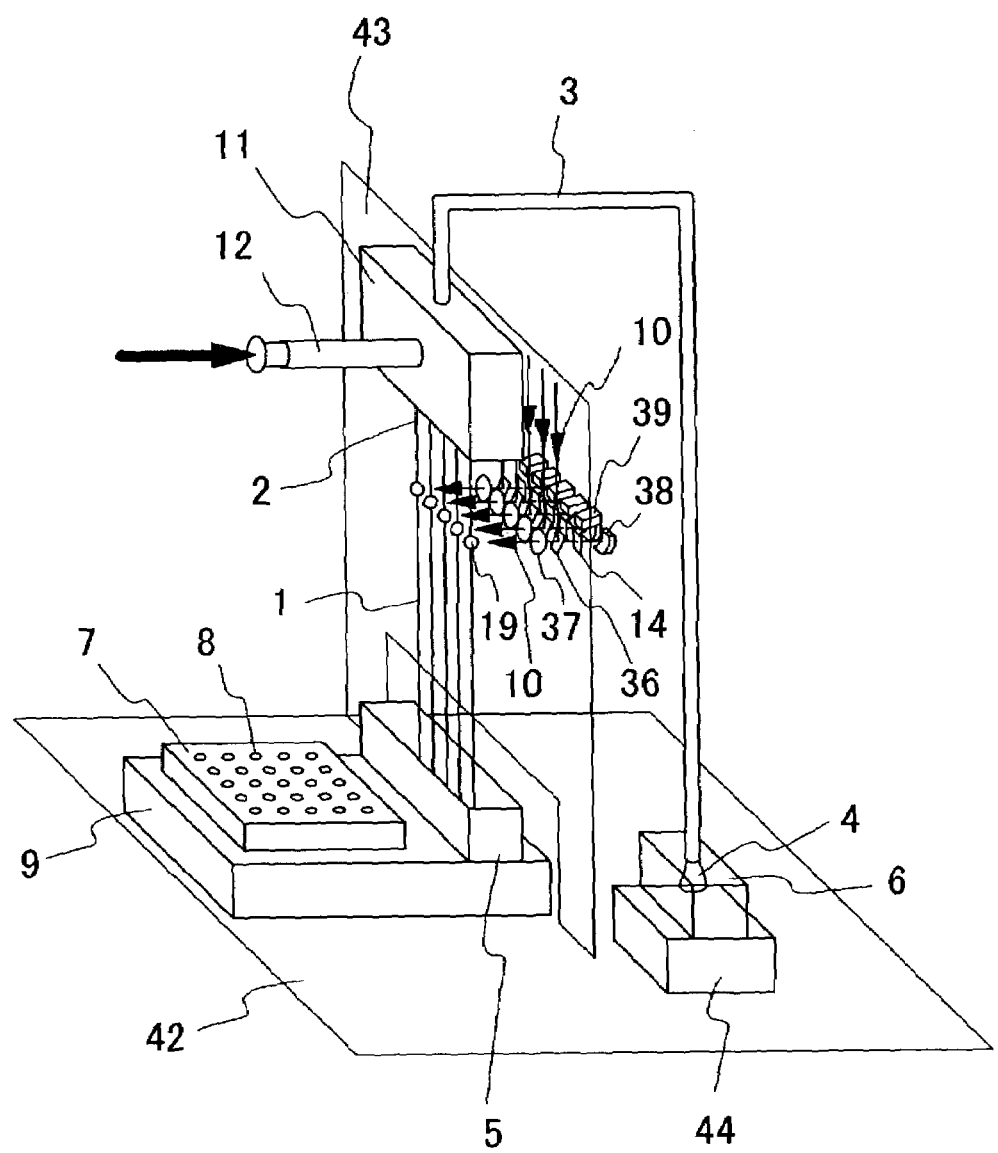
FIG. 5 is a perspective view illustrating an example of an entire constitution for a second device of Example 1 according to this invention.

FIG. 5 is a perspective view illustrating an example of an entire constitution for a second device of Example 1 according to this invention. In the second device of Example 1, a laser irradiation system and a fluorescence detection system are changed in the constitution for the first device of Example 1. As shown in FIG. 5, when the laser irradiation system and the fluorescence detection system are disposed in parallel on every capillary, the fluorescence from each of the capillaries can be measured under an identical condition making the quartz cell unnecessary. Further, in the constitution shown in FIG. 5, the distance for the arrangement of the capillaries is optional and may be widened, and the capillaries may be used in any plurality of numbers.

Figure 6:
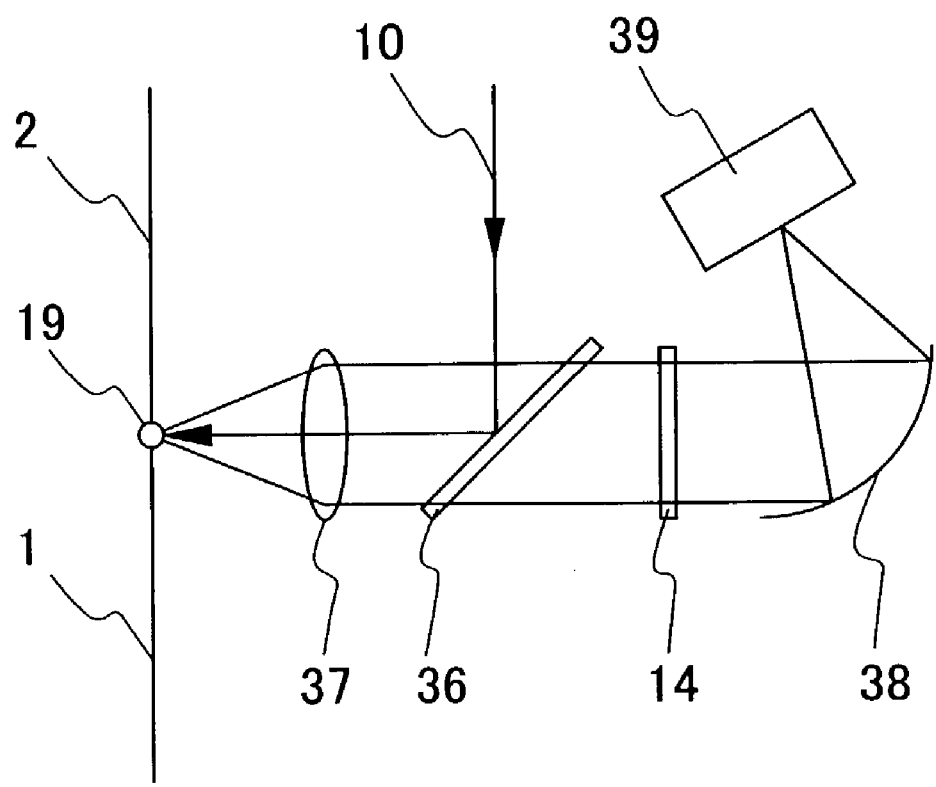
FIG. 6 is a cross sectional view illustrating an example of a constitution of an optical system for a second device of Example 1 according to this invention.

FIG. 6 is a cross sectional view illustrating an example of a constitution of an optical system for a second device of Example 1 according to this invention (cross sectional view vertical to a plane on which capillaries are arranged and including an axis for the capillary, which represents a single laser irradiation system and fluorescence detection system. A laser beam 10 entered vertically from above is reflected on a dichroic mirror 36, condensed through an objective lens 37 and then irradiated to a fluorescence detection position 19 for the capillary.

The fluorescence emitted from the fluorescence detection position 19 is condensed through the objective lens 37 into a parallel luminous flux, permeates the dichroic mirror 36, permeates a laser light rejective filter 14, and then reflect on a grating 38. The reflected light is focused on a 1-dimensional CCD camera 39 while undergoing wavelength dispersion. The direction of arranging the pixels of the 1-dimensional CCD camera 39 is aligned with the direction of the wavelength dispersion. The laser beam irradiation system and the fluorescence detection system are corresponded each by one to one capillary and arranged at an identical distance (9 mm) in parallel with the line along which the fluorescence detection positions 19 are arranged. The width of one laser beam system and fluorescence detection system along the direction of the line on which the fluorescence detection positions 19 are arranged is designed to be 9 mm or less.

In the second device of Example 1, laser beams are required with the same number as that for the capillaries; that is, twelve laser beams are required. Twelve laser light sources may be used or a single laser beam may be split into twelve beams. Further, like that in FIG. 1, it may be adapted to a constitution of using a single laser beam to collectively irradiate the entire capillaries, and conduct fluorescence detection on every capillary as shown in FIG. 5.

Figure 7:
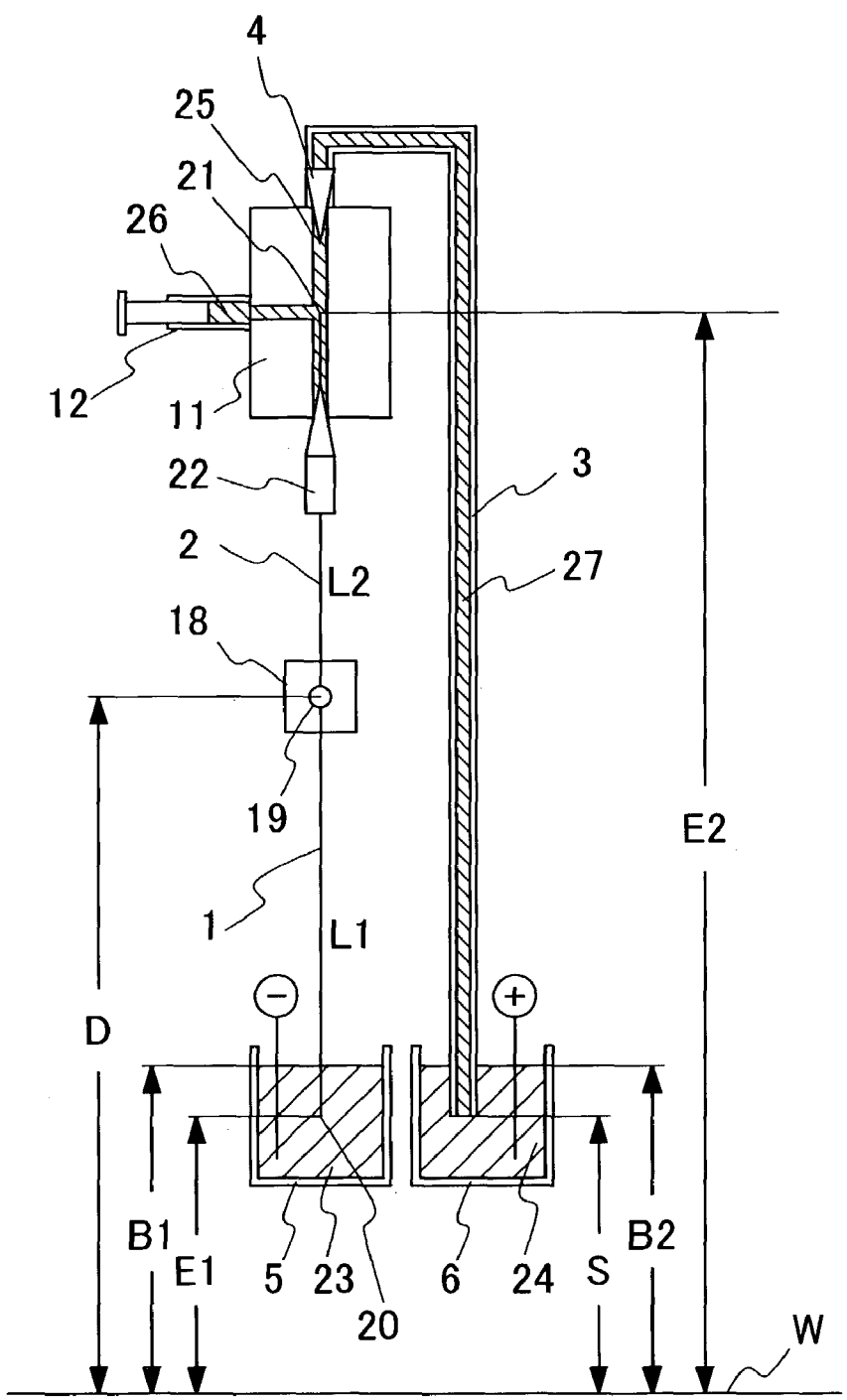
FIG. 7 is a side elevation view illustrating a third device of Example 1 according to this invention.

FIG. 7 is a side elevational view for a third device of Example 1 according to this invention. In the constitution shown in FIG. 1 to FIG. 3 and FIG. 5, the pressure resistant valve 4 is disposed at the top end of the connection tube 3. In this device, however, the pressure resistant valve 4 is disposed to the connection portion between the pump block 11 and the connection tube 3 as shown in FIG. 7. With the constitution shown in FIG. 7, the connection tube is no longer necessary to have pressure resistant performance and the system can be constituted simply and conveniently.

EXAMPLE 2

Figure 8:
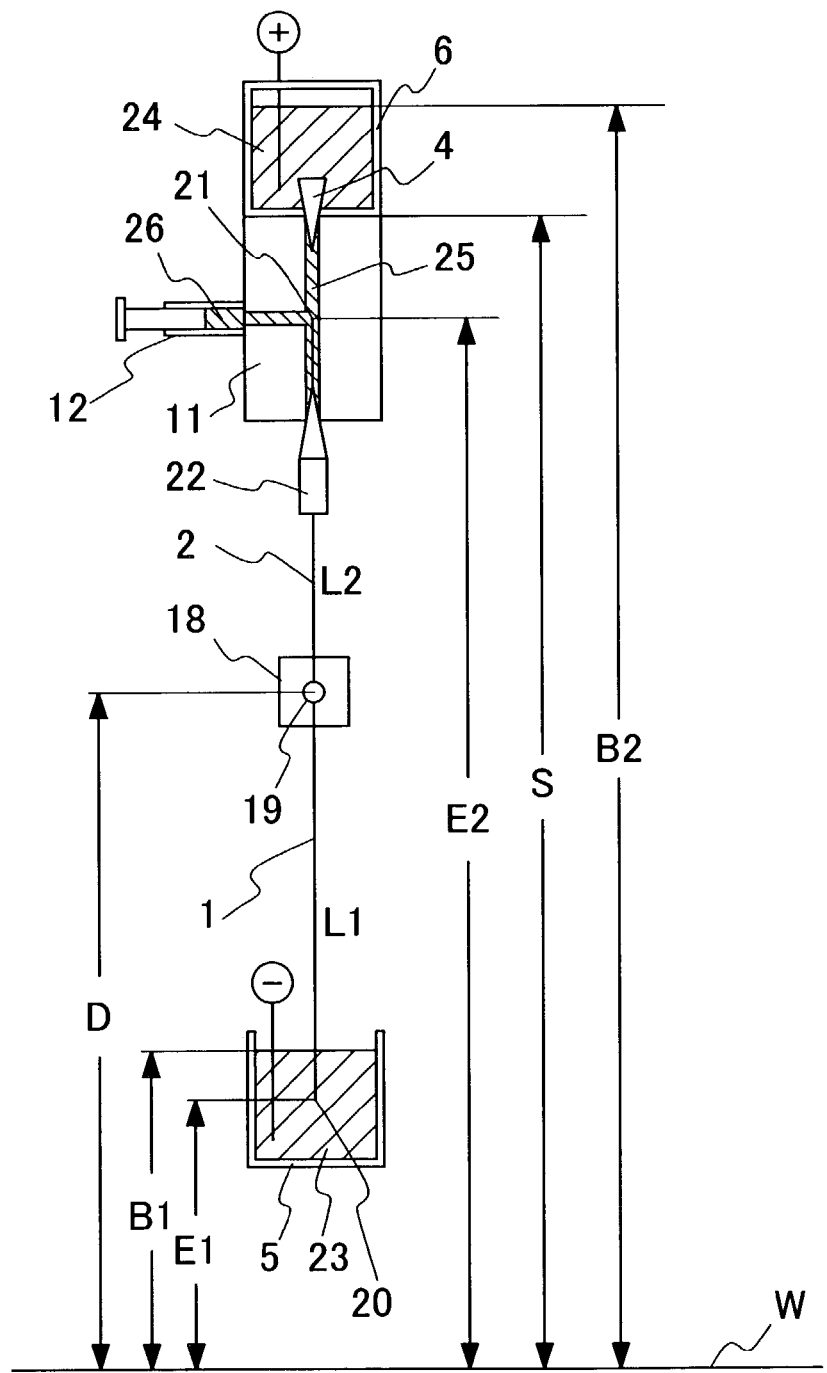
FIG. 8 is a side elevation view illustrating an example of a constitution for a first device of Example 2 according to this invention.

FIG. 8 is a side elevational view illustrating a constitution for a first device of Example 2 according to this invention (viewed from the direction identical with that in FIG. 3). The capillary size and the arrangement of a plurality of capillaries and a pump block 11 are identical with those shown in FIG. 1 to FIG. 3, and the conditions for relation 2 to relation 4 are satisfied. As shown in FIG. 8, the pump block 11 and an anode buffer vessel 6 are connected directly with a pressure resistant valve 4 and without using a connection tube 3. As a result, the liquid level of the anode buffer 24 is higher than the liquid level of the cathode buffer 23 and the condition for the relation 1 is not satisfied. If the liquid surface of the anode buffer 24 and the liquid surface of the cathode buffer level 23 are exposed to an atmospheric pressure, the anode buffer 24, the polymer solution 25 in the pump block, the polymer solution in the capillary and the cathode buffer 23 are dropped from the higher level to the lower level in a flow channel formed of them. In the capillary, the polymer solution moves from the sample elution end 21 to the sample injection end 20. Since the movement of the polymer solution in the capillary gives an undesired effect on the electrophoretic performance, it is necessary to avoid the movement.

In the constitution shown in FIG. 8, dropping of the solution is prevented by tightly closing the anode buffer vessel 6. This is conducted because when the solution drops, air in the anode buffer vessel 6 expands to lower the pressure to less than a normal pressure near the liquid level of the cathode buffer 23. Accordingly, as the initial air volume in the anode buffer vessel 6 is smaller, the dropping preventive effect is larger. However, even when the initial air volume is decreased, gas is evolved from the anode along with electrophoresis to increase the air (gas) volume in the anode buffer vessel 6.

Figure 9:
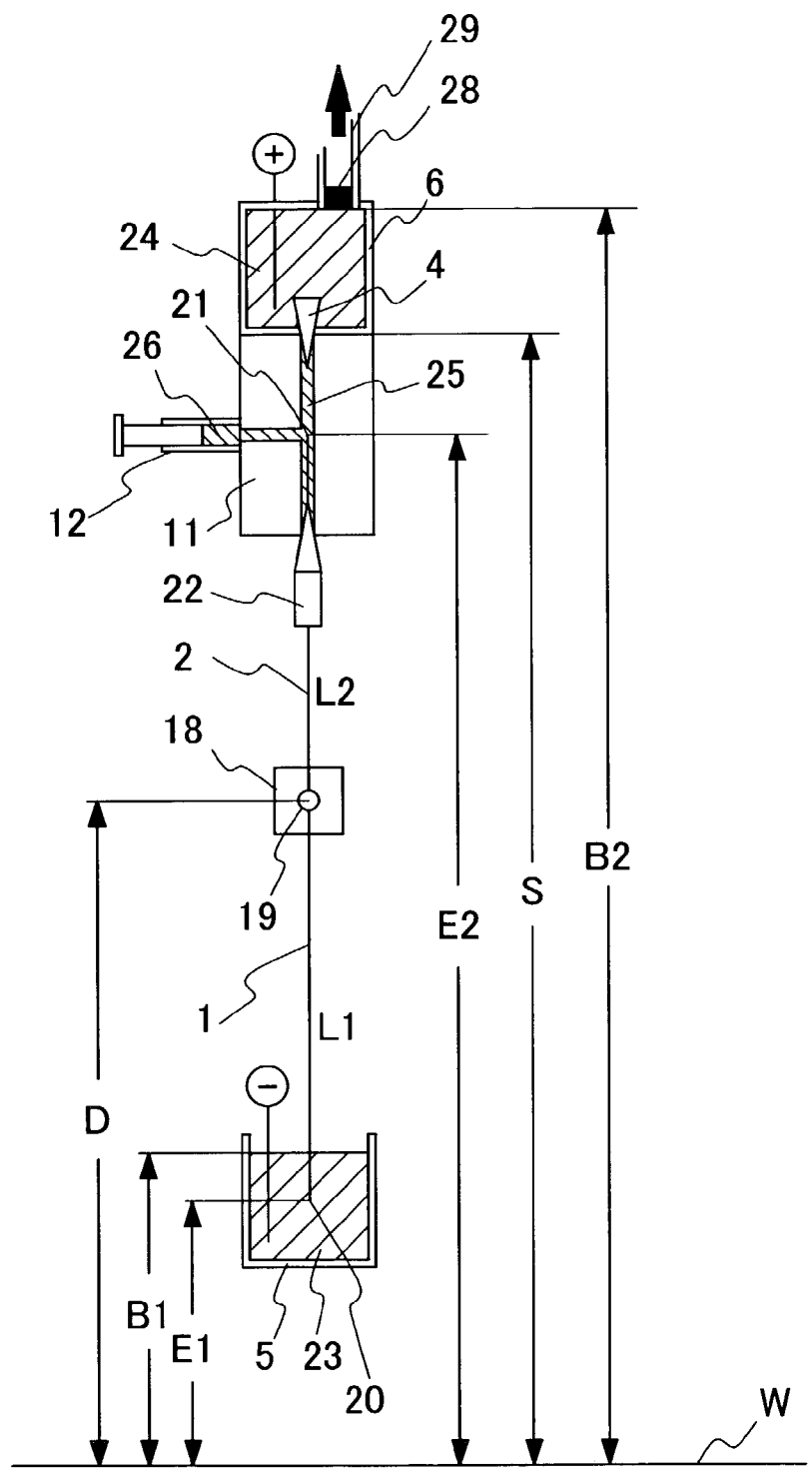
FIG. 9 is a side elevation view illustrating an example of a constitution for a second device of Example 2 according to this invention.

FIG. 9 is a side elevational view illustrating an example of a constitution for a second device of Example 2 according to this invention. In the example shown in FIG. 9, air in the anode buffer vessel 6 in the constitution shown in FIG. 8 is positively removed. An air vent hole is disposed to a tightly closed anode buffer vessel 6 and air in the anode buffer vessel 6 is sucked by way of a tetrafluoroethylene resin membrane filter 28 and a suction tube 29 by a pump (not illustrated).

Since the tetrafluoroethylene resin membrane filter 28 has a property of permeating gases but not permeating a liquids, only the gas evolved upon electrophoresis can be removed selectively without removing the anode buffer itself. Other polymeric membranes having the same property (gas permeating membrane) as the tetrafluoroethylene resin membrane may also be used. Dropping of solution can be suppressed by the constitution described above more effectively than by the constitution described in FIG. 8.

Similar effects for preventing dropping of the solution may be obtained also by tightly closing the cathode buffer vessel 5 in which the sample injection end is placed and, when gases in the cathode buffer vessel 5 are removed by using a tetrafluoroethylene resin membrane filter, a more effect can be obtained. Further, the anode buffer vessel 16 may also be closed tightly together.

Figure 10:
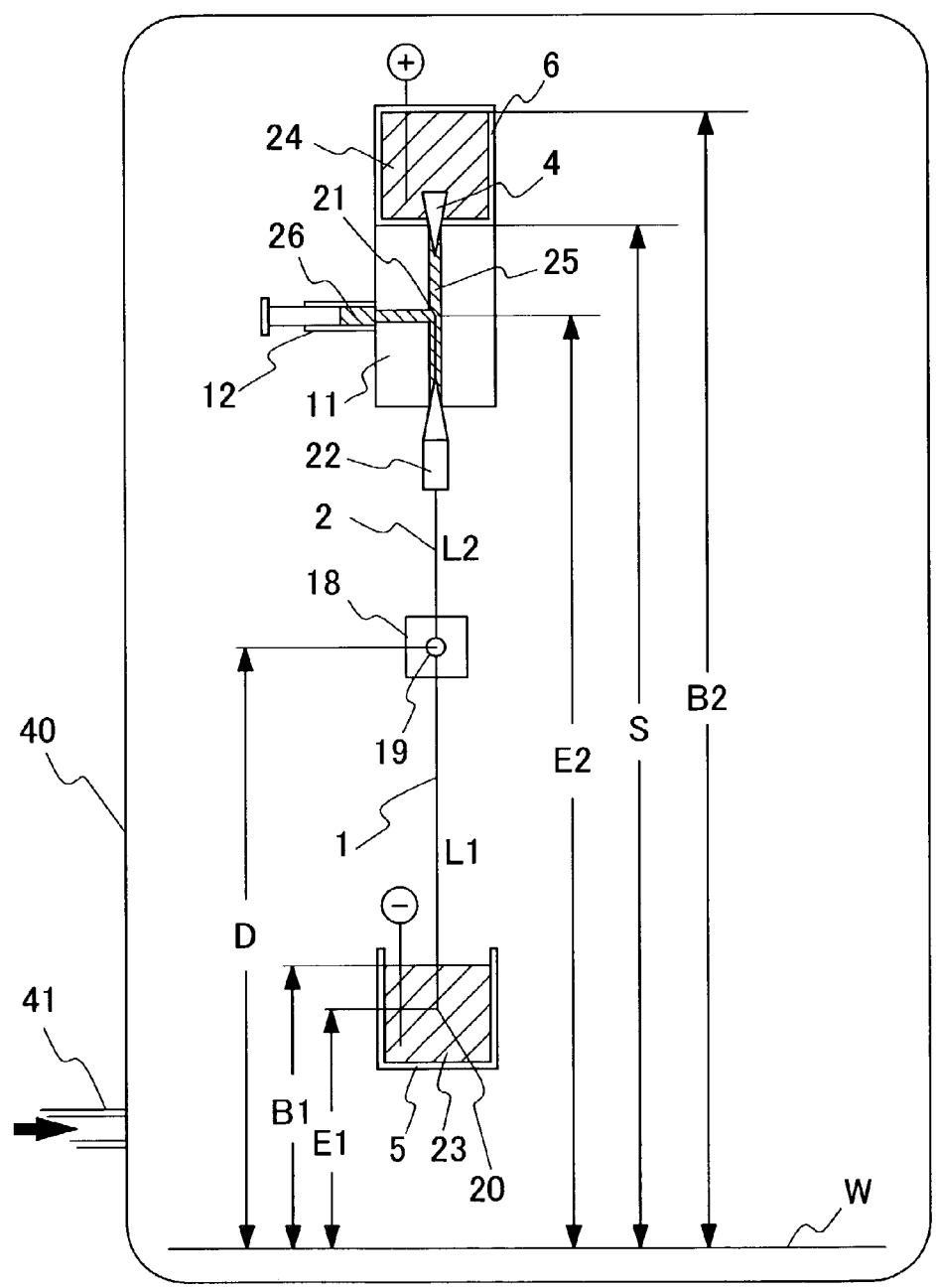
FIG. 10 is a side elevation view illustrating an example of a constitution for a third device of Example 2 according to this invention.

FIG. 10 is a side elevational view illustrating an example of a constitution for a third device of Example 2 according to this invention. In the constitution shown in FIG. 10, a pressure higher than the normal pressure (atmospheric pressure) is applied to the liquid surface of the cathode buffer solution 23 in the constitution of the system shown in FIG. 8. The cathode buffer vessel 5 to which the sample injection end is placed and the vicinity thereof may be disposed in a tightly closed container, or the entire system may be disposed in a tightly closed container 40 as shown in FIG. 10.

Air is supplied through a pressurizing tube 41 by using a pump (not illustrated) into the tightly closed container 40 in which the cathode buffer vessel 5 and the vicinity thereof are placed to increase the pressure in the tightly closed container 40 and apply a pressure higher than the atmospheric pressure to the liquid surface of the cathode buffer 23. The pressure higher than the atmospheric pressure reaches a cathode buffer 23, a polymer solution in a capillary, the polymer solution 25 in a pump block 11 and an anode buffer 24 to put the entire solution under a high pressure. As a result, evolvement of gases from the solutions can be suppressed and, at the same time, dropping of the solution can be inhibited more effectively, thereby enabling stable and high resolution electrophoresis. The constitution for the laser irradiation system and the fluorescence detection system can be identical with that in Example 1.

EXAMPLE 3

In the capillary electrophoresis using the polymer solution, the capillary itself undergoes a temperature change by the generation of heat in the capillary or fluctuations in the circumstantial temperature, by which the volume of the polymer solution in the inside may possibly be increased or decreased. As a result, the polymer solution moves in the capillary to sometimes deteriorate the electrophoresis performance. Accordingly, it is extremely effective to control the temperature of the capillary for preventing the degradation of the electrophoresis performance. Further, electrophoresis performance such as resolution and speed can be provided fully by controlling the temperature of the capillary to a predetermined temperature.

In Example 1, the temperature of the capillary is controlled by blowing temperature controlled air to the capillaries. Temperature control by an air flow is difficult since the temperature or blowing speed of air varies depending on the position of the capillaries. In Example 3, a different temperature control system is to be explained.

Figure 11:
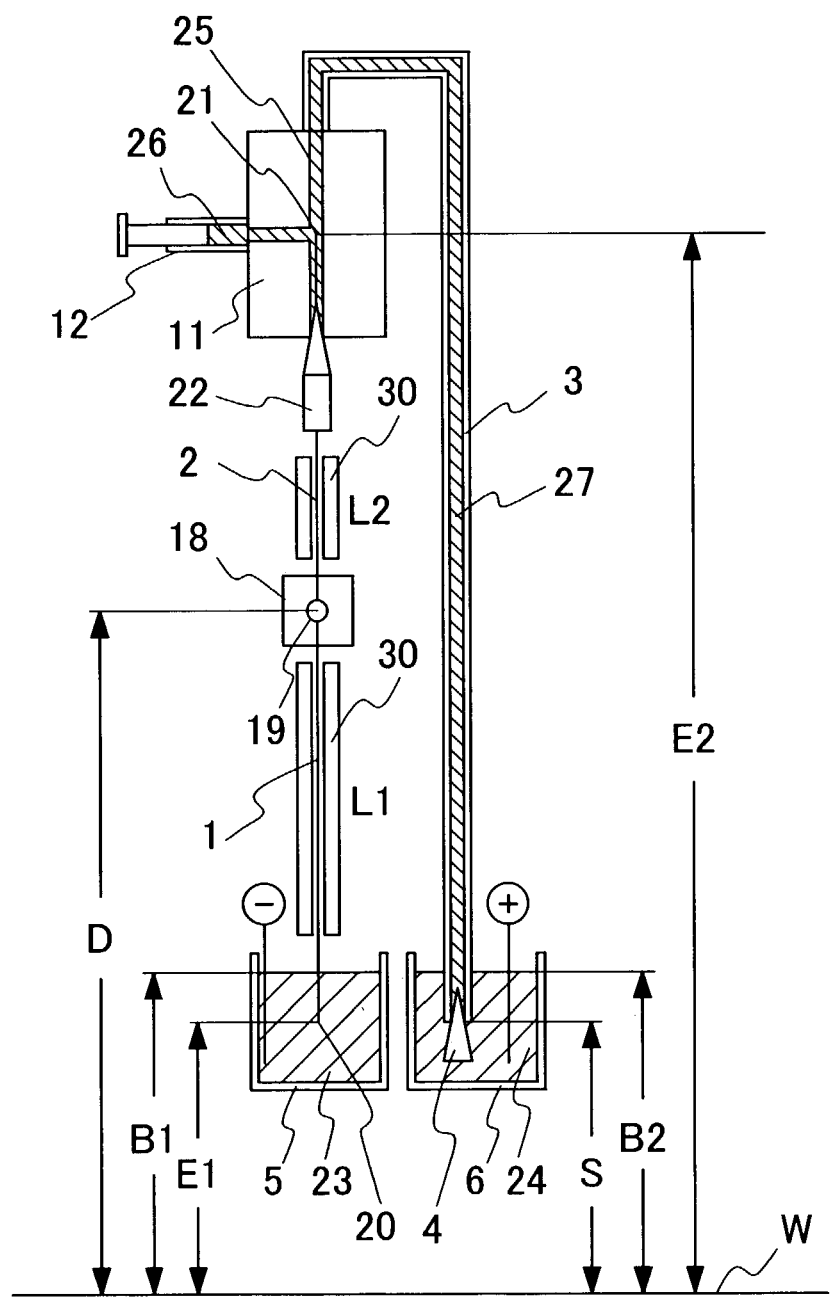
FIG. 11 is a side elevation view illustrating an example of a constitution for a first device of Example 3 according to this invention.

FIG. 11 is a side elevational view illustrating an example of an constitution for a first device of Example 3 according to this invention (as viewed from the direction identical with that in FIG. 3). In FIG. 11, a constitution for the temperature control of the capillary different from that in Example 1 is added to the constitution shown in FIG. 1 to FIG. 3.

The separation part 1 and the sample elution part 2 of the capillary are respectively put between two temperature control plates 30 of high heat conductivity and the temperature control plates 30 are in contact with the capillary. The temperature control plate 30 is connected with a heater and a cooler (not illustrated) to control the temperature control plate 30 and the capillary at a portion in contact with the temperature control plate 30 to a predetermined temperature.

As the ratio of the length of the region of the capillary under temperature control relative to the entire length of the capillary (L1+L2) (temperature control cover rate) gets higher, the stability and resolution of electrophoretic separation are improved. In the constitution shown in FIG. 11, the separation part 1 and the sample elution part 2 are divisionally put between the temperature control plates 30 respectively.

If the portion near the fluorescence detection position 19 is put between the temperature control plates 30, fluorescence measurement can not be conducted, so that the portion near the fluorescence detection position 19 can not be controlled with the constitution shown in FIG. 11. Furthermore, since the vicinity of the sample injection end has to be immersed in the cathode buffer 23 or the sample solution, the temperature of a region of the capillary at least for several centimeters from the sample injection end 20 can not be controlled. Therefore, when the effective separation length L1 is decreased, the temperature control cover rate is lowered to sometimes deteriorate the electrophoresis performance.

Figure 12:
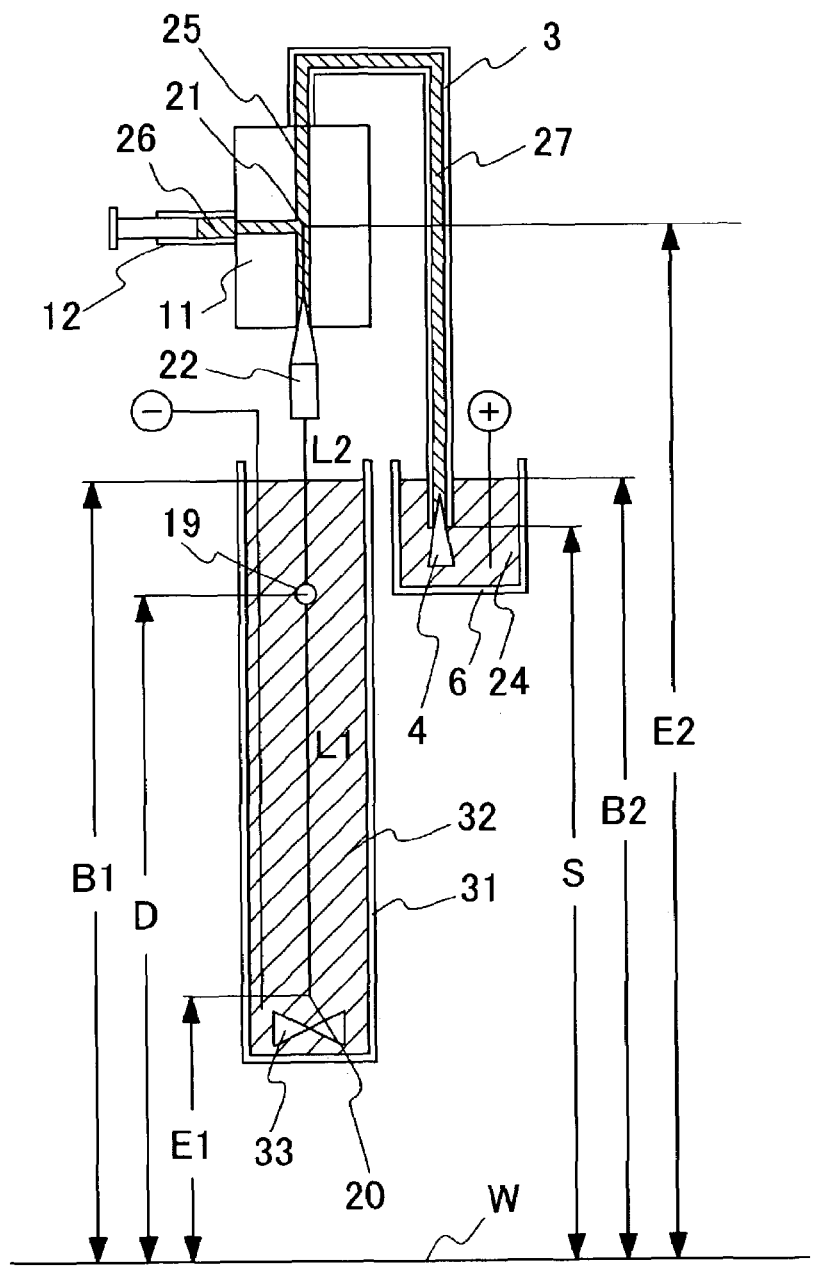
FIG. 12 is a side elevation view illustrating an example of a constitution for a second device of Example 3 according to this invention.

FIG. 12 is a side elevational view illustrating an example of a constitution for a second device of Example 3 according to this invention (viewed from the direction identical with that in FIG. 3). In the constitution shown in FIG. 12, a constitution for the temperature control different from that of FIG. 11 is adapted. In the embodiment shown in FIG. 12, the size of the capillary, arrangement of a plurality of capillaries are identical with those of the constitution shown in FIG. 1 to FIG. 3. The cathode buffer vessel is formed as a deep vessel, to constitute a temperature controlled cathode buffer vessel 31 capable of controlling the temperature of the cathode buffer.

The temperature controlled cathode buffer 32 in the temperature controlled cathode buffer vessel 31 is circulated and controlled by an incorporated heater/cooler 33 to a predetermined temperature. The entire separation part 1 and a portion of the sample elution part 2 of the capillary are immersed in the temperature controlled cathode buffer 32 and the temperature of the capillary at the immersed portion is controlled. In this embodiment, the fluorescence detection position 19 of the capillary is completely immersed in the temperature controlled cathode buffer 32.

When the constitution shown in FIG. 12 is used, the temperature control cover rate can be increased even with a short effective electrophoretic separation length L1 so that electrophoresis at a high resolution can be conducted stably.

For making the height identical between the liquid level of the temperature controlled cathode buffer 32 and the liquid level of the anode buffer 24, the length of the connection tube is decreased and the anode buffer vessel 6 is placed at a higher position compared with the constitution shown in FIG. 3.

Since the fluorescence detection position 19 of the capillary is within the temperature controlled cathode buffer 32 (B1>D), fluorescence measurement is conducted through the temperature controlled cathode buffer 32 and the wall of the temperature controlled cathode buffer vessel 31. The wall of the temperature controlled cathode buffer vessel 31 is preferably made of a colorless and transparent material emitting fluorescence as less as possible, for example, quartz glass.

The basic constitution of the laser irradiation system and the fluorescence detection system in the second device of Example 3 may be identical with that of FIG. 5 and FIG. 6. Different from the constitution showing FIG. 6, since the wall of the temperature controlled cathode buffer vessel 31 and the temperature controlled cathode buffer 32 are present between an objective lens 37 and the fluorescence detection position 19, it is necessary to align the focal distance by controlling the position of the objective lens 37.

When the temperature controlled cathode buffer vessel 31 containing the temperature controlled cathode buffer 32 shown in FIG. 12 is applied to the constitution shown in FIG. 8, FIG. 9 or FIG. 10, the temperature control cover rate can be increased even with the short effective separation length L1 in the same constitution as shown in FIG. 12 and electrophoresis at high separation performance can be conducted stably.

In Examples 1 to Example 3 explained above, a plurality of capillaries are arranged in parallel with each other at an identical distance on one identical plane. As has been described above, a constitution of using a single capillary may of course be adopted in Example 1 to Example 3 as explained above.

EXAMPLE 4

Figure 13:
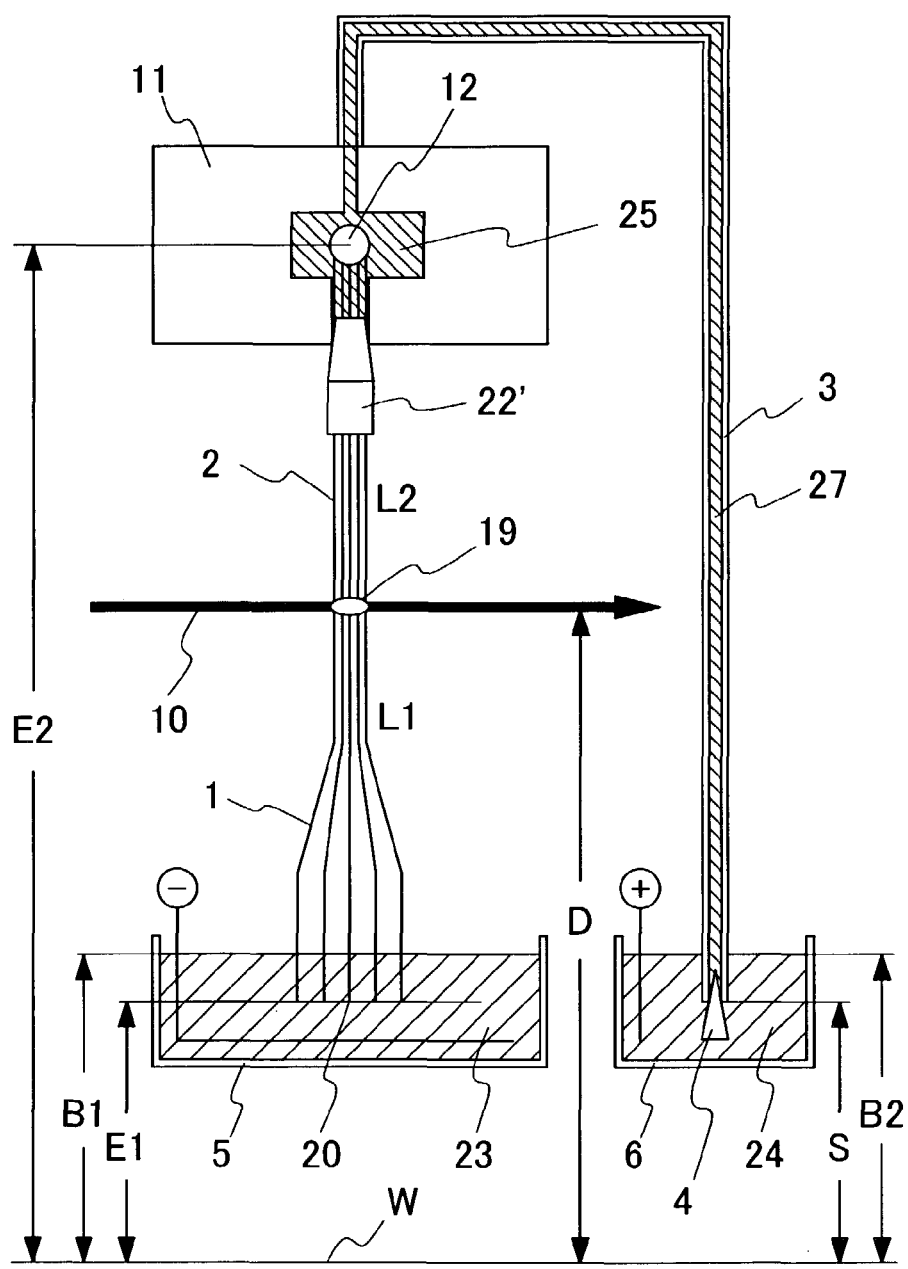
FIG. 13 is a front elevation view illustrating an example of a constitution for a device of Example 4 according to this invention.

FIG. 13 is a front elevational view illustrating an example of a constitution for a device of Example 4 according to this invention (as viewed from the direction identical with that in FIG. 2). The distance for the arrangement of capillaries is changed between the sample injection ends 20 and the fluorescence detection positions 19. The size of the capillary, and the number of capillaries are identical with those in Example 1. For the sake of simplicity, only five capillaries are shown like that in FIG. 2. Each of the fluorescence detection positions 19 is arranged on one identical line on the laser beam 10 and arranged so as to be in close adjacent position with each other.

The pitch of arrangement is 0.36 mm, and the entire width for the arrangement is 5.4 mm at the fluorescence detection positions 19 of the capillary. The sample injection ends 20 for respective capillaries are arranged on one identical line at a pitch of arrangement of 4.5 mm and for the entire width of arrangement of 99.5 mm. The separation part 1 and the sample elution part 2 near the fluorescence detection positions 19 of the respective capillaries are arranged so as to be present on a plane in parallel with the sheet of the drawing for FIG. 13. Accordingly, FIG. 13, as viewed from the right in the sheet of the drawing is substantially identical with FIG. 3.

The sample elution end 21 of each capillary is connected with a pump block 11 by using a connector 22'. The connector 22' is a male thread made of a plastic material having a small hole at a center of such a size as to allow twelve capillaries to just pass therethrough and having a pointed conical shape at the top end. Twelve capillaries are inserted each at a predetermined length into the hole of the male thread, and a gap between the inner wall for the hole of the male thread and each of the capillaries is filled and secured with an adhesive such as Araldite. As a result, the gap between the inner wall for the hole of the male thread and each of the capillaries is sealed.

The pump block 11 is formed with a female thread hole tapered so as to match the male thread, and the top end of the female thread hole is in communication with an internal space of the pump block 11 in which the polymer solution 25 is filled. When the male thread is clamped into the tapered female thread hole in a state where the twelve capillaries are passed through into the tapered female thread hole, the top end of the male thread is deformed. As a result, a gap between the connector 22' and the pump block 11 is sealed.

Since the all of the regions from the fluorescence detection positions 19 to the sample injection ends 20 of the respective capillaries are arranged on one identical plane, temperature can be controlled in the same manner as in the constitution shown in FIG. 11. That is, twelve capillaries are put between two temperature control plates simultaneously and the temperature of the twelve capillaries can be controlled.

Since the separation parts 1 of the respective capillaries are arranged on one identical plane, the effective separation length of the capillary disposed at the central position in the array is somewhat shorter than the capillary disposed on both ends in the array. The pitch for the arrangement of 4.5 mm is equal with the pitch of arrangement in the 384 hole micro titer plate in which sample solution vessels are arranged in a 32×24 lattice. Accordingly, the sample injection ends 20 of the twelve capillaries can be inserted at once into respective different sample solution vessels of the micro titer plate and the samples can be injected simultaneously.

In the constitution shown in FIG. 13, different from the constitution in FIG. 2, since the fluorescence detection positions 19 for the respective capillaries are arranged in close relation with each other, laser irradiation and fluorescence detection are easy and effective.

Figure 14:
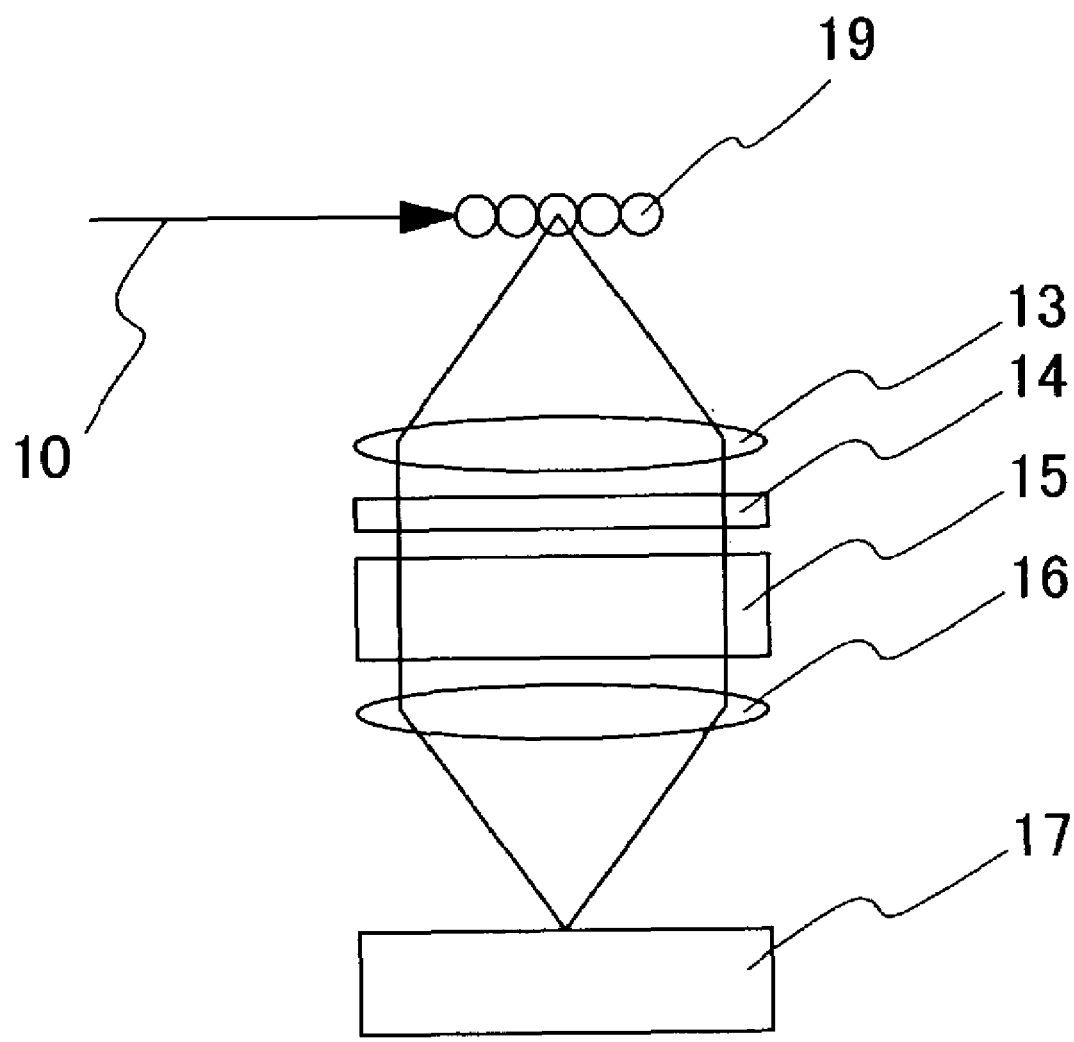
FIG. 14 is a cross sectional view illustrating an example of a constitution of an optical system for the device of Example 4 according to this invention.

FIG. 14 is a cross sectional view illustrating an example of a constitution of an optical system of a fluorescence detection device for the device of Example 4 according to this invention (cross sectional view vertical to the axes of capillaries, including the fluorescence detection positions 19). A laser beam 10 is condensed through a lens (not illustrated) and irradiated along a line on which fluorescence detection positions 19 are arranged from the lateral side of the plane on which the respective capillaries are arranged, by which the fluorescence detection positions 19 for all of the twelve capillaries can be irradiated simultaneously with the laser beam 10 (Anal. Chem. 68, 2699-2704 (1996) (Prior art 4)).

Fluorescence emitted from the samples moving under electrophoresis in the respective capillaries are detected simultaneously from the direction vertical to the plane on which the respective capillaries are arranged. The fluorescence is detected by the same constitution as that shown in FIG. 1 and, since the fluorescence detection positions 19 are in close relation with each other, fluorescence from each of the capillaries can be detected efficiently.

Further, as the laser irradiation method, the following methods may also be used. A laser beam is diverged by using a cylindrical lens in a direction of a line on which the fluorescence detection positions 19 are arranged to irradiate twelve capillaries simultaneously (Anal. Chem. 66, 1424-1431 (1994) (prior art 5)). Further, the laser beam is condensed through a lens, the beam is scanned to irradiate the fluorescence detection positions 19 of the capillaries successively (Anal. Chem. 64, 2149-2154 (1992) prior art 6).

EXAMPLE 5

Figure 15:
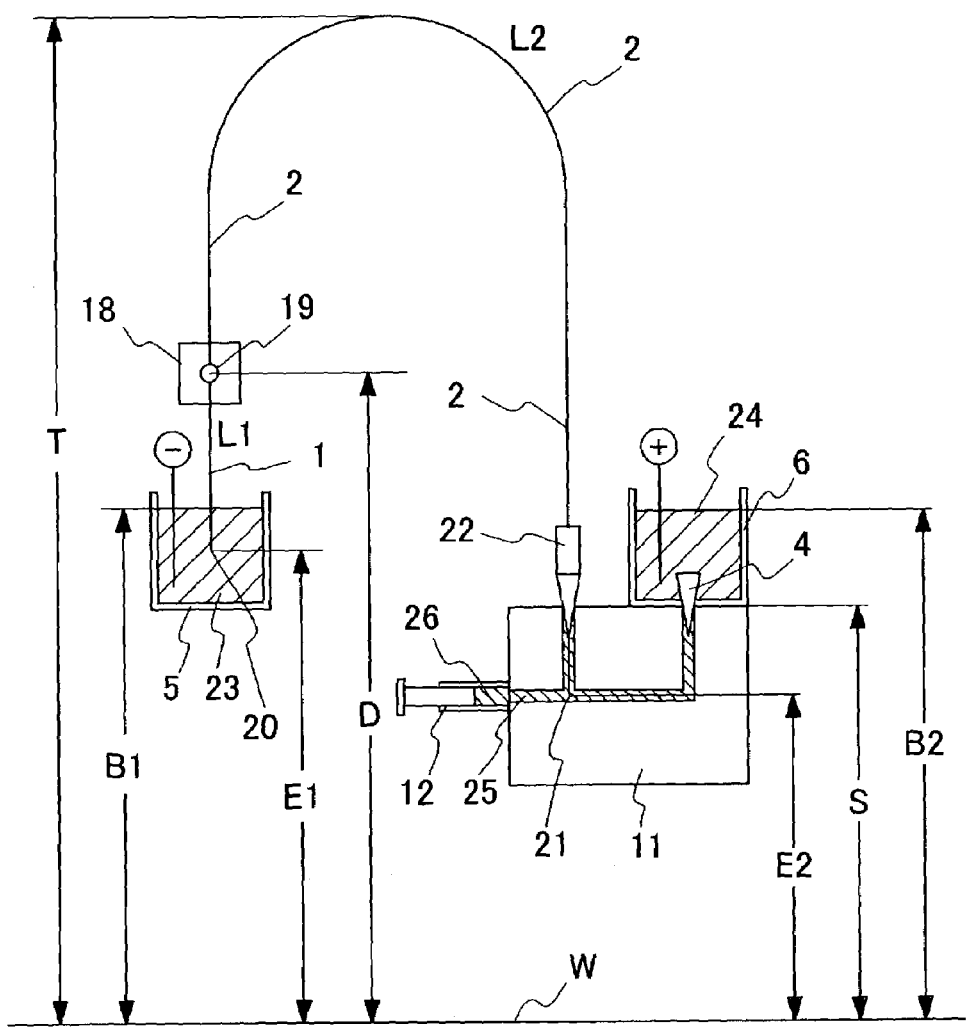
FIG. 15 is a side elevation view illustrating an example of a constitution for a device of Example 5 according to this invention.
Figure 16:
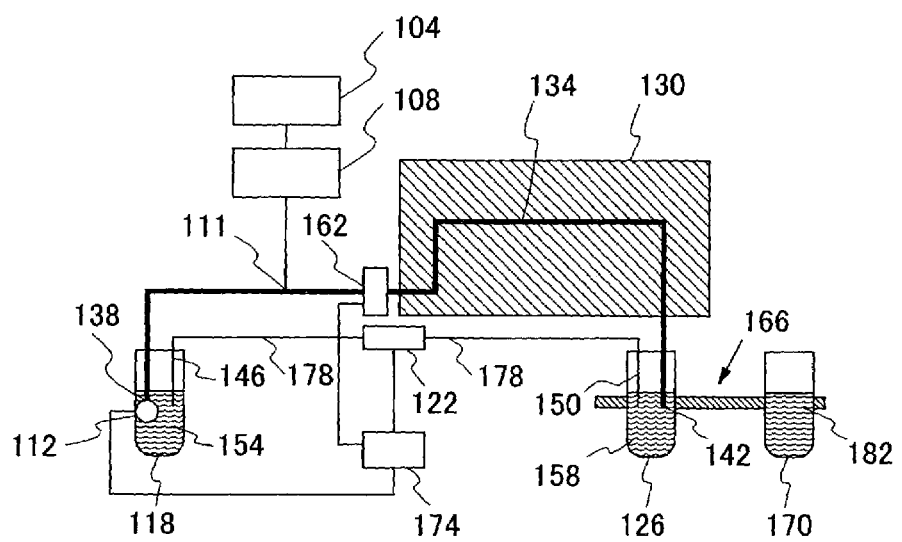
FIG. 16 is a view explaining a constitution of an electrophoresis system in the prior art using a single capillary.

FIG. 15 is a side elevational view illustrating an example of a constitution for a device of Example 5 according to this invention (as viewed from the direction identical with that in FIG. 3). In the constitution of Example 5, capillaries are arranged differently from the constitution shown in Example 1 to Example 4 where all regions for the respective capillaries are arranged in parallel with a vertical line.

This capillary has a 360 cm outer diameter, 50 cm inner diameter and 60 cm entire length in which a detection window is disposed at a position 10 cm from the sample injection end 20 (50 cm from the sample elution end 4) to constitute a fluorescence detection position 19 (L1=10 cm, L2=50 cm).

The constitution of the device of Example 5 has a feature in the relation: L1<L2.

The capillary is arranged such that the sample injection end 20 of the capillary is pointed downward vertically, and the axis of the capillary of the separation part 1 and a portion of the sample elution part 2 near the fluorescence detection position 19 are substantially in parallel with a vertical line. The capillary is arranged such that a middle portion of the sample elution part 2 of the capillary forms an upward convex loop, in which the height at the highest point of the capillary (apex) from the reference horizontal plane W is T.

The sample elution end 21 of the capillary is in pressure resistant connection with a pump block 11 using a connector 22 in the same manner as in the constitution shown in FIG. 2. The pump block 11 is connected with a gas tight syringe 12 and connected with a anode buffer vessel 6 by way of a pressure resistant valve 4.

Since the sample elution length L2 is sufficiently large, the height for the pump block 11 and the anode buffer vessel 6 can be adjusted such that the height of the liquid levels are identical between the cathode buffer 23 and the anode buffer 24. As a result, the condition shown by the relation 1 can be satisfied and movement of the polymer solution in the capillary can be prevented. In the constitution of Example 5, the conditions shown in the relation 1, relation 2 and relation 5 can be satisfied. While a single capillary is used in Example 5, a plurality of capillaries may be arranged at an irregular or identical distance in the constitution of Example 5.

With the constitution of the system according to this invention, capillary electrophoresis with shorter effective separation length than that in the prior art can be conducted stably, ultra high speed electrophoresis can be conducted and high throughput and high performance electrophoresis is also possible by arranging a plurality of capillaries into an array.

Electrophoresis with short effective separation length is enabled with a constitution of holding a polymer solution filled in a capillary in a stable state, irradiating a laser beam during movement of the sample introduced from the sample injection end vertically from downward to upward in the capillary and detecting the fluorescence emitted from the sample.

Electrophoresis at ultra high speed is enabled by shortening the effective separation length of capillary electrophoresis to 10 cm or less thereby enabling sequencing for 200 base length in about 10 min and electrophoresis with ultra high throughput can be attained by arranging a plurality of capillaries into an array.

Although the invention has been described in its preferred form with a certain degree of particularity, it is understood that the present disclosure of the preferred form has been changed in the details of construction and the combination and arrangement of parts may be resorted to without departing from the spirit and the scope of the present invention.

What is claimed is:

1. A capillary electrophoresis system comprising:
a lane, at least a part of which includes at least one capillary for separating fluorescent-labeled samples by electrophoresis by applying a voltage across a sample injection end and a sample elution end of the capillary;
an irradiation unit for irradiating a laser beam to the capillary;

a detection unit for detecting fluorescence emitted from the samples that are electrophoretically separated, wherein the capillary satisfies a relation: T−E1>L1, where T is a height for a highest position of the capillary in a vertical direction from a reference horizontal plane, E1 is a height for the sample injection end of the capillary in the vertical direction from the reference horizontal plane, and L1 is a length of a section of the capillary between the sample injection end and a fluorescence detection position at which the laser beam is irradiated, the capillary is filled with a polymer solution during the electrophoresis, and one end of the lane and another end of the lane are immersed in a first buffer and a second buffer, respectively, a height of a liquid level of the first buffer is substantially identical with a height of a liquid level of the second buffer during the electrophoresis.

2. A capillary electrophoresis system according to claim 1, wherein the sample injection end is substantially pointed vertically downward.

3. A capillary electrophoresis system according to claim 1, wherein the capillary satisfies a relation: L1≦L2, where L2 is a length of a section of the capillary between the fluorescence detection position and the sample elution end.

4. A capillary electrophoresis system according to claim 1, wherein the capillary satisfies a relation: E2≦D, where E2 is a height of the sample elution end from the horizontal reference plane, and D is a height of fluorescence detection position from the horizontal reference plane.

5. A capillary electrophoresis system according to claim 1, further comprising electrophoretic separation medium controlling means for introducing an electrophoretic separation medium into the capillary and for removing the electrophoretic separation medium from the capillary.

6. A capillary electrophoresis system according to claim 1, wherein a plurality of capillaries are provided.

7. A capillary electrophoresis system according to claim 1, wherein both of the irradiation unit and the detection unit are disposed corresponding to each of the capillaries.

8. A capillary electrophoresis system according to claim 7, wherein the plurality of capillaries are disposed such that corresponding fluorescence detection positions thereof are arranged close to each other and substantially in one line.

9. A capillary electrophoresis system according to claim 7, wherein the plurality of capillaries are arranged substantially on one vertical plane.

10. A capillary electrophoresis system comprising:

a lane, at least one part of which includes at least one capillary for separating fluorescent-labeled samples by electrophoresis by applying a voltage across a sample injection end and a sample elution end of the capillary;

an irradiation unit for irradiating a laser beam to the capillary;

a detection unit for detecting fluorescence emitted from the samples that are electrophoretically separated, wherein the capillary has a fluorescence detection position at which a laser beam is irradiated, and movements of the samples at the fluorescence detection position is substantially directed vertically upward, the capillary is filled with a polymer solution during the electrophoresis, and one end of the lane and another end of the lane are immersed in a first buffer and a second buffer, respectively, a height of a liquid level of the first buffer is substantially identical with a height of a liquid level of the second buffer during the electrophoresis.

11. A capillary electrophoresis system according to claim 10, wherein the sample injection end is substantially pointed vertically downward.

12. A capillary electrophoresis system according to claim 10, wherein the capillary satisfies a relation: L1≦L2, where L2 is a length of a section of the capillary between the fluorescence detection position and the sample elution end.

13. A capillary electrophoresis system according to claim 10, wherein the capillary satisfies a relation: E2≦D, where E2 is a height of the sample elution end from the horizontal reference plane, and D is a height of fluorescence detection position from the horizontal reference plane.

14. A capillary electrophoresis system according to claim 10, further comprising electrophoretic separation medium controlling means for introducing an electrophoretic separation medium into the capillary and for removing the electrophoretic separation medium from the capillary.

15. A capillary electrophoresis system according to claim 10, wherein a plurality of capillaries are provided.

16. A capillary electrophoresis system according to claim 15, wherein both of the irradiation unit and the detection unit are disposed corresponding to each of the capillaries.

17. A capillary electrophoresis system according to claim 15, wherein the plurality of capillaries are disposed such that corresponding fluorescence detection positions thereof are arranged close to each other and substantially in one line.

18. A capillary electrophoresis system according to claim 15, wherein the plurality of capillaries are arranged substantially on one vertical plane.

* * * * *